US007725517B1

(12) United States Patent
Keenan

(10) Patent No.: US 7,725,517 B1
(45) Date of Patent: May 25, 2010

(54) METHODS FOR SPECTRAL IMAGE ANALYSIS BY EXPLOITING SPATIAL SIMPLICITY

(75) Inventor: Michael R. Keenan, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1187 days.

(21) Appl. No.: 11/233,223

(22) Filed: Sep. 22, 2005

Related U.S. Application Data

(60) Provisional application No. 60/614,867, filed on Sep. 29, 2004.

(51) Int. Cl.
*G06F 7/38* (2006.01)
*G01N 31/00* (2006.01)
(52) U.S. Cl. .................................. 708/446; 702/23
(58) Field of Classification Search ............... 708/446, 708/520, 607; 702/22, 23
See application file for complete search history.

(56) References Cited

U.S. PATENT DOCUMENTS

| 6,584,413 | B1 | 6/2003 | Keenan et al. |
| 6,675,106 | B1 | 1/2004 | Keenan et al. |
| 6,842,702 | B2 * | 1/2005 | Haaland et al. ............... 702/18 |
| 7,451,173 | B1 * | 11/2008 | Van Benthem et al. ...... 708/607 |
| 2004/0126892 | A1 * | 7/2004 | Bogomolov et al. ........ 436/161 |

OTHER PUBLICATIONS

Michael R. Keenan, "Accounting for Poisson noise in the multivariate analysis of ToF-SIMS spectrum images," Surface and Interface Analysis, 2004, 36, 203-212.

Michael W. Browne, "An Overview of Analytic Rotation in Exploratory Factor Analysis," Multivariate Rehavioral Research, 36 (1), 111-150, 2001.

M. Forina, "Methods of Varimax Rotation in Factor Analysis with Applications in Clinical and Food Chemistry," Journal of Chemometrics, vol. 3, 1988, 115-125.

Daniel D. Lee, "Learning the parts of objects by non-negative matrix factorization," Nature, vol. 401, Oct. 21, 1999, 788-791.

(Continued)

*Primary Examiner*—Chuong D Ngo
(74) *Attorney, Agent, or Firm*—Kevin W. Bieg

(57) ABSTRACT

Several full-spectrum imaging techniques have been introduced in recent years that promise to provide rapid and comprehensive chemical characterization of complex samples. One of the remaining obstacles to adopting these techniques for routine use is the difficulty of reducing the vast quantities of raw spectral data to meaningful chemical information. Multivariate factor analysis techniques, such as Principal Component Analysis and Alternating Least Squares-based Multivariate Curve Resolution, have proven effective for extracting the essential chemical information from high dimensional spectral image data sets into a limited number of components that describe the spectral characteristics and spatial distributions of the chemical species comprising the sample. There are many cases, however, in which those constraints are not effective and where alternative approaches may provide new analytical insights.

For many cases of practical importance, imaged samples are "simple" in the sense that they consist of relatively discrete chemical phases. That is, at any given location, only one or a few of the chemical species comprising the entire sample have non-zero concentrations. The methods of spectral image analysis of the present invention exploit this simplicity in the spatial domain to make the resulting factor models more realistic. Therefore, more physically accurate and interpretable spectral and abundance components can be extracted from spectral images that have spatially simple structure.

14 Claims, 16 Drawing Sheets

OTHER PUBLICATIONS

Paul Sajda, "Recovery of constituent spectra using non-negative matrix factorization," Proceedings of SPIE vol. 5207 Wavelets: Applications in Signal and Image Processing X, 2003.

Michael R. Keenan, "A Method for Exploiting Bias in Factor Analysis Using Constrained Alternating Least Squares Algorithms," U.S. Appl. No. 10/794,538, filed Mar. 4, 2004.

Michael R. Keenan, "Spectral Compression Algorithms for the Analysis of Very Large Multivariate Images," U.S. Appl. No. 10/772,548, filed Feb. 4, 2004 (related to U.S. Appl. No. 10/772,805, filed Feb. 4, 2004).

Rasmus Bro, "Improving the speed of multiway algorithms Part II: Compression," Chemometrics and Intelligent Laboratory Systems 42, 1998, 105-113.

Mark H. Van Benthem, "Fast Cominatorial Algorithm for the Solution of Linearly Constrained Least Squares Problems," U.S. Appl. No. 10/938,444, filed Sep. 9, 2004.

* cited by examiner

METHODS FOR SPECTRAL IMAGE ANALYSIS BY EXPLOITING SPATIAL SIMPLICITY

CROSS-REFERENCE TO RELATED APPLICATION

This application claims the benefit of U.S. Provisional Application No. 60/614,867, filed Sep. 29, 2004, which is incorporated herein by reference.

STATEMENT OF GOVERNMENT INTEREST

This invention was made with Government support under contract no. DEAC04-94AL85000 awarded by the U.S. Department of Energy to Sandia Corporation. The Government has certain rights in the invention.

FIELD OF THE INVENTION

The present invention relates to spectral image analysis and, in particular, to methods for spectral image analysis by exploiting spatial simplicity.

BACKGROUND OF THE INVENTION

Several full-spectrum imaging techniques have been introduced in recent years that promise to provide rapid and comprehensive chemical characterization of complex samples. These spectroscopic imaging techniques include Electron Probe Microanalysis (EPMA), Scanning Electron Microscopy (SEM) with attached Energy Dispersive X-Ray Spectrometer (EDX), X-Ray Fluorescence (XRF), Electron Energy Loss spectroscopy (EELS), Particle Induced X-ray Emission (PIXE), Auger Electron Spectroscopy (AES), gamma-ray spectroscopy, Secondary Ion Mass Spectroscopy (SIMS), X-Ray Photoelectron Spectroscopy (XPS), Infrared Spectroscopy (IR), Raman Spectroscopy, Magnetic Resonance Imaging (MRI) scans, Computerized Axial Tomography (CAT) scans, IR reflectometry, Mass Spectrometry (MS), multidimensional chromatographic/spectroscopic techniques, hyperspectral remote imaging sensors, etc. These new spectroscopic imaging systems enable the collection of a complete spectrum at each point in a 1-, 2- or 3-dimensional spatial array. It is not uncommon that these spectral image data sets comprise tens of thousands of individual spectra, or more.

One of the remaining obstacles to adopting these techniques for routine use is the difficulty of reducing the vast quantities of raw spectral data to meaningful chemical information. Multivariate factor analysis techniques have proven effective for extracting the essential chemical information from high dimensional spectral image data sets into a limited number of components that describe the spectral characteristics and spatial distributions of the chemical species comprising the sample. In mathematical terms, given an m-pixel×n-channel matrix of spectral data D, we wish to approximate D by the matrix factorization $$D \cong CS^T \tag{1}$$

Here, C is an m-pixel×p-component matrix describing the distribution of the pure components at each spatial location and S is an n-channel×p-component matrix representation of the pure-component spectra. In the typical case that p<<m and n, the factorization in Eq. (1) accomplishes a large reduction in the dimensionality of the data set with the goal of optimally separating factors embodying real chemical information from those describing only noise.

It is well known, however, that factor-based methods suffer from a "rotational ambiguity." Given any invertible p×p transformation matrix R, D can be equally well expressed as $$D \cong CS^T = (CR)(R^{-1}S^T) = \tilde{C}\tilde{S}^T \tag{2}$$

That is, an infinite number of factor pairs $\tilde{C}$ and $\tilde{S}$ will provide equally good fits to the data. The key to deriving relatively unique factors, then, is to select those factor solutions that satisfy additional optimization criteria. Thus, physically inspired constraints are often employed to derive relatively unique factor models that make the pure components more easily interpretable. In general, one would expect that the extent to which these criteria or constraints actually reflect the physical reality of a given sample, the higher the fidelity and reliability of the derived components.

Principal Component Analysis (PCA), used either by itself or to preprocess data, is the most ubiquitous tool of factor analysis. The constraints imposed by PCA are that the spectral and concentration factors must contain orthogonal components and that the components serially maximize the variance in the data that each accounts for. Neither constraint has any basis in physical reality; thus, the factors obtained via PCA are abstract and not easily interpreted. Alternating Least Squares-based Multivariate Curve Resolution (MCR-ALS) is another common factorization method used for spectral image analysis. This technique may force spectra and concentrations to be non-negative, for instance, yielding more physically realistic pure components. There are many cases, however, in which those constraints are not effective and where alternative approaches may provide new analytical insights.

For many cases of practical importance, imaged samples are "simple" in the sense that they consist of relatively discrete chemical phases. That is, at any given location, only one or a few of the chemical species comprising the entire sample have non-zero concentrations. In the limiting case that each location has only a single chemical component having non-zero concentration, the sample is said to be "perfectly simple." The methods of the present invention exploit this simplicity in the spatial domain to make the resulting factor models more realistic. Therefore, more physically accurate and interpretable spectral and abundance components can be extracted from spectral images that have spatially simple structure.

SUMMARY OF THE INVENTION

The present invention is directed to methods for spectral image analysis that exploit spatial simplicity. A method comprises providing a matrix of spectral image data; factoring the data matrix into the product of a matrix of orthogonal scores vectors and a matrix of orthonormal loading vectors using PCA; determining a rotation matrix; rotating the spatial-domain loading matrix to provide a simplified rotated loading matrix; and inverse rotating the scores matrix to provide estimates of the pure-component spectra. The rotation matrix can be determined using an Orthomax procedure. In particular, rotation of the orthonormal spatial factors arising from PCA can be effective for estimating physically acceptable and easily interpretable pure-component spectra and abundances for spectral images that approximate perfectly simple structure. Furthermore, the rotated factor solutions can be refined to provide pure components that satisfy physically prescribed constraints, such as, non-negativity of spectra and abundances. For example, the rotated loading matrix and the rotated scores matrix can be further refined using constrained least squares, constrained alternating least squares, or non-negative matrix factorization approaches.

Alternatively, spatial simplicity can be imposed as an additional constraint during MCR-ALS procedures. Accordingly, a method for spectral image analysis comprises providing a matrix of spectral image data; obtaining an initial estimate for a spectral shapes matrix; selecting elements of zero abundance in the concentration matrix; obtaining a least squares estimate for the concentration matrix, subject to the zero-equality constraints at the zero abundance matrix elements in addition to standard constraints such as non-negativity at the remaining abundance matrix elements; and obtaining a least squares estimate for spectral shapes matrix, subject to constraints. Either the number or location of the elements to have zero abundance can be selected. These steps can be iterated for a predetermined number of iteration loops or until an acceptable level of convergence is achieved.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 1(a) shows the measured spectral image (top) and the true pure-component spectra (bottom). FIG. 1(b) shows the standard PCA solution. FIG. 1(c) shows the corresponding PC2 vs PC1 plot (top) and estimated pure-component spectra (bottom) for the spatially rotated PCA solution.

FIG. 2(a) shows a spectral image (top) and a mean spectrum (bottom) for the simulation of a perfectly simple spatial structure, wherein each pixel in the spectral image was assigned to only one of the four chemical phases (Fe—Ni—Co, Cu, Ag, and Ti). FIG. 2(b) shows the true pure-component spectra and abundance maps for each phase.

FIG. 4(a) shows the estimated pure-component spectra obtained from a standard MCR-ALS analysis of the sample. FIG. 4(b) shows the estimated spectra obtained from a spatially rotated PCA, wherein the principal components were unweighted and re-orthogonalized prior to rotation.

FIG. 4(c) shows the estimated spectra obtained from a spatially rotated PCA, wherein the principal components were rotated in the weighted space and the rotated factors were subsequently unweighted. FIG. 4(d) shows the estimated spectra, after unweighting and refinement of the spatially rotated PCA using the non-negative matrix factorization method of Sajda et al. FIG. 4(e) shows the estimated spectra, after refinement of the spatially rotated PCA in the weighted space using the full data matrix and the maximum-likelihood-based, non-negative matrix factorization method of Lee and Seung. FIG. 4(f) shows the estimated spectra, after refinement of the spatially rotated PCA in the weighted space using a factored representation of the data matrix and an adaptation of the method of Lee and Seung.

FIG. 13(a) shows the estimated pure-component spectra and abundance maps obtained when the fraction of zeros in the abundance maps was constrained to equal 33%. FIG. 13(b) shows the estimated pure-component spectra and abundance maps obtained when the fraction of zeros in the abundance maps was constrained to equal 42%. FIG. 13(c) shows the estimated pure-component spectra and abundance maps obtained when the fraction of zeros in the abundance maps was constrained to equal 50%.

FIG. 14(a) shows the total abundance histogram when the pure-component spectra were estimated by standard MCR-ALS. FIG. 14(b) shows the total abundance histogram when the pure-component spectra were estimated by simplicity-constrained MCR-ALS with 42.25% of the abundance elements constrained to equal zero. FIG. 14(c) shows the total abundance histogram when the pure-component spectra were estimated by simplicity-constrained MCR-ALS with 49.95% of the abundance elements constrained to equal zero.

FIG. 15(a) is a schematic of the MEMS device and FIG. 15(b) is the mean XPS spectrum. FIG. 15(c) shows the view of the MEMS device, obtained in an SEM, from the ion gun used to clean an oxide from the surface.

DETAILED DESCRIPTION OF THE INVENTION

Figure 1:
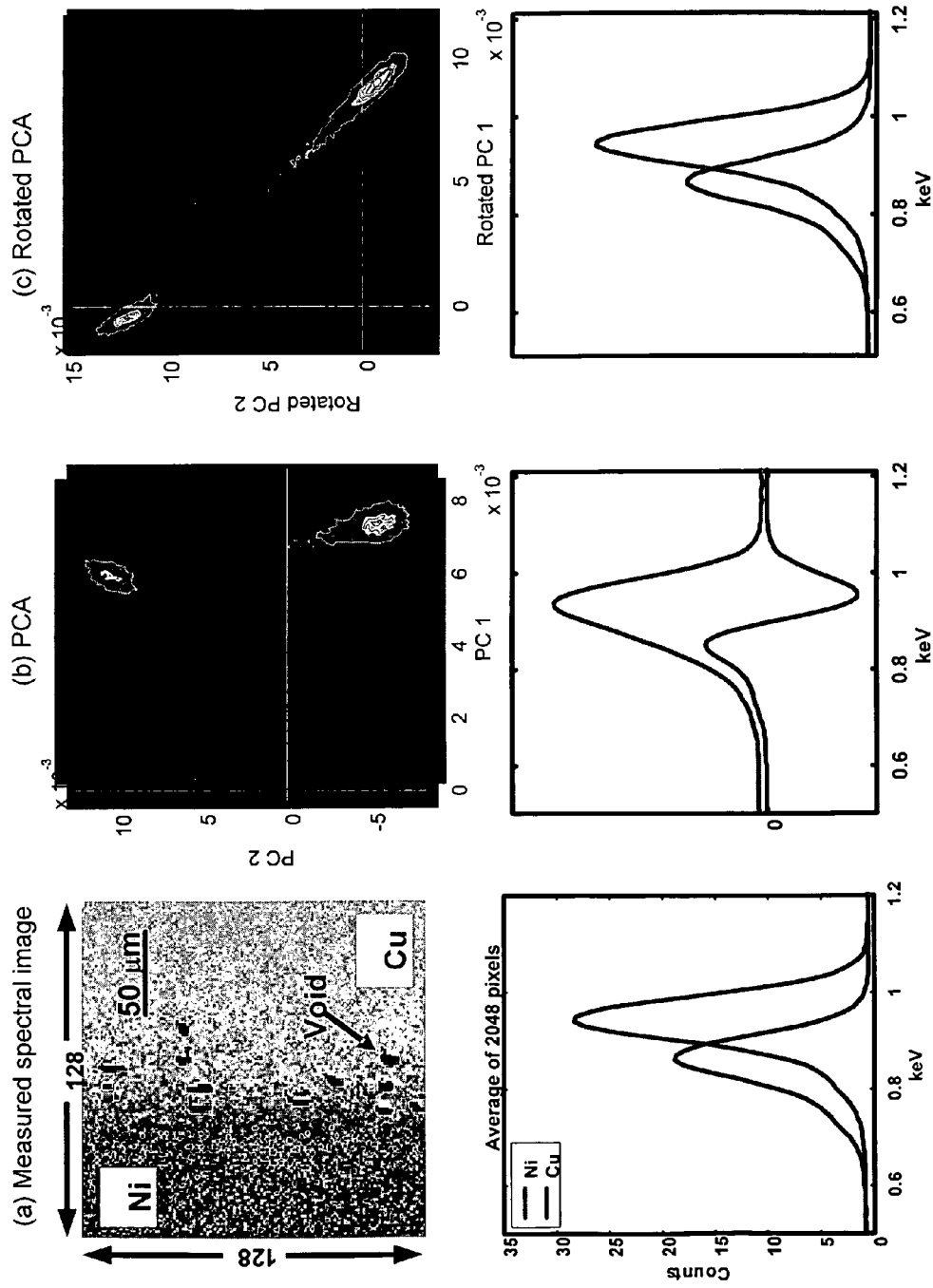
FIG. 1 shows a comparison between the PCA and the spatially rotated PCA factor solutions for an uncomplicated two-component spectral image of a Cu/Ni diffusion couple that was imaged by Energy Dispersive X-ray (EDS) analysis in a scanning electron microscope.

In general, multivariate spectral analysis for chemical characterization of a sample can include: determining the number of chemical species (pure elements and chemical phases or alloys) that comprise an inhomogeneous mixture being imaged; extracting the spectra of these "pure" components (elements or phases); quantifying the amount or concentration of each component present in the sample; and mapping the spatial distribution of these components across the sample.

In general, an image can comprise any arbitrary, multidimensional array of points. The image can include a spatial dimension, such as lines, traditional 2D images, or 3D volumes; or a temporal dimension, such as a time series of images. For example, in the case of a gas chromatography/mass spectroscopy (GC/MS) image, the dimension is a separation coordinate. The multivariate image analysis techniques will be described herein in reference to a spatial dimension. However, it is understood that the techniques can be applied also to non-spatial images, such as those comprising a time series or chromatographic coordinate.

Multivariate spectral analysis can be performed on a full spectrum image that can be represented as a two-dimensional data matrix D. The two-dimensional data matrix D can be obtained by unfolding a measured multidimensional spectral data set. For example, the multidimensional spectra data set $\underline{D}$ can be a data cube that comprises a 1D spectrum at each pixel on a 2D spatial grid corresponding to the (X,Y) coordinates of the pixel's location. The 2D data matrix D enables the easy and efficient use of standard linear algebra and matrix operations.

The data matrix D can be factored into the product of two matrices, C and $S^T$, according to Eq. (1), where D has dimensions of m×n, and m is the number of pixels and n is the number of spectral channels. The matrix C is a concentration matrix, which is related to the concentration of the chemical phases (e.g., a matrix representing a map of the pure-component abundances) and has dimensions of m×p, where p is the number of pure components. The matrix S is a spectral shapes matrix, which contains information about the spectral shapes of the pure chemical components (e.g., a matrix of the pure-component spectra). S has dimensions n×p.

The factorization of Eq. (1) can be accomplished by an image analysis of D. A number of prior image analysis methods are described in U.S. Pat. Nos. 6,584,413 and 6,675,106 to Keenan and Kotula, which are incorporated herein by reference. A spectral-image factorization method based on PCA has also been described. See M. R. Keenan and P. G. Kotula, *Surf. Interface Anal.* 36, 203 (2004), which is incorporated herein by reference.

If desired, the measured data matrix D can be weighted, depending on the type of experiment being analyzed, and depending on the properties of the noise or background signal generated during data acquisition. Weighting is generally used whenever the properties of the noise are not uniform throughout the measurement space (i.e., heteroscedastic noise). This is particularly true in the case of "counting" experiments in which the noise is characterized as following a Poisson probability distribution in which the magnitude of the uncertainty varies with the magnitude of the signal. For multi-channel data acquisition the noise is not characterized by a single probability distribution, but rather, by a distribution whose parameters will, in principle, differ from channel to channel and from pixel to pixel within a channel. Additionally, heteroscedasticity can also arise from other effects, e.g., non-uniform detector responses, or mathematical transformations applied to the data (e.g., taking logarithms).

Weighting is also useful when there is a large disparity between the total number of counts (e.g., observations) arising from different elements or phases (e.g., a sample comprising a small amount of contaminant located on top of a substrate made of a single material). Weighting, therefore, is useful for accurately identifying minor phases, trace elements, or subtle gradients in composition across a sample. By properly accounting for experimental noise characteristics, chemically relevant features having small numbers of counts can become more significant, in a least squares sense, than large magnitude noise associated with major spectroscopic features.

Weighting can also be used to account for data "outliers". Data outliers can include malfunctioning energy channels or pixel elements in a detector array. For example, a dead (i.e., inoperative) energy channel (e.g., zero signal) can be effectively removed from the data matrix D by assigning a sufficiently small weight. Alternatively, for detectors that use a CCD pixel array, an occurrence of a "hot" (i.e., saturated) or dead pixel can be weighted in a similar fashion, namely, by assigning a sufficiently small weight.

Therefore, data matrix D can be weighted to create a weighted data matrix $\tilde{D}$, according to $$\tilde{D} = GDH \qquad (3)$$

where G is a pre-multiply weighting matrix having dimensions m×m; and H is a post-multiply weighting matrix having dimensions n×n. In general, G is used to weight the row-space of D, and H is used to weight the column-space of D. Obviously, the weighting matrices G and H can be the identity matrix if no weighting is desired.

The matrix G can be used to account for unequal variance in the observations from pixel to pixel, independent of channel number (i.e., energy or wavelength). For example, weighting by G could be used in the case where there are hot or dead pixels, or if there was an array detector where different detector elements had different noise properties. Weighting by G also could be used in the situation where there were much higher total counts in some pixels as compared to others, caused, for example, by unequal dwell times.

The matrix H can account for unequal variance in the observations from channel to channel, independent of pixel location. For example, weighting by H could be used when the noise level varies from one energy channel to the next. For X-ray detection in spectral analysis, the noise will be higher on average in channels that have greater signal on average due to the Poisson nature of a counting experiment.

Spectral image analysis of the weighted data matrix $\tilde{D}$ yields $\tilde{C} = GC$, which is the weighted concentration matrix, and $\tilde{S}^T = S^T H$, which is the weighted spectral shapes matrix. The corresponding unweighted concentrations and spectra can be recovered as $C = G^{-1}\tilde{C}$ and $S^T = \tilde{S}^T H^{-1}$, respectively. For simplicity, the analysis of the unweighted data matrix D will be described hereinafter, although it will be understood that the method of the present invention can also be applied to the weighted data matrix.

Spectral Image Analysis by Spatially Rotated PCA

PCA is one of the core techniques of multivariate statistical analysis and it has been employed in numerous and diverse applications including dimensional reduction, data compression, exploratory data analysis, factor analysis, pattern recognition, classification, and multivariate calibration. In particular, PCA can be used in the analysis of hyperspectral image data. See P. Geladi and H. Grahn, *Multivariate Image Analysis*, Wiley, Chinchester, UK (1996).

The goal of PCA is to extract the useful information in a high-dimension data set into a lower dimension subspace. From a geometric point of view, PCA begins by finding that single direction in the n-dimensional space that best describes the location of the data. The vector describing that direction is the first principal component. Once found, a second direction, orthogonal to the first, is determined that best accounts for the variation in the data that is orthogonal to the first. This is the second principal component. The process continues with each new principal component maximally accounting for the variation in the data that is orthogonal to all preceding components. The first few principal components will contain the chemical information of interest. If there are p such principal components, the remaining n−p principal components are assumed to describe experimental noise or error. Limiting further analysis to the p-dimensional subspace defined by the first p principal components provides the desired dimensional reduction and data compression.

In matrix terms, PCA is concerned with factoring a data matrix D into the product of two other matrices, a scores matrix T whose columns are mutually orthogonal and a matrix P of orthonormal loading vectors, according to $$D = TP^T \quad (4)$$

To take a spectroscopic example, the loading vectors P describe the spectral characteristics of the chemical constituents of a sample and the scores T are related to their concentrations. The data set is then seen to be described as a linear combination of basis spectra. An alternative point of view can be obtained by performing PCA on the transposed data matrix $D^T$:

$$D^T = \overline{T}\overline{P}^T \quad (5)$$

In this case, the orthonormal loading vectors $\overline{P}$ describe the spatial or abundance characteristics of the data and the scores $\overline{T}$ are related to the spectra. The data is now being represented as a linear combination of basis images. These two approaches are dual and the respective loading vectors span the same space, namely, that of the spectral data.

The close connection between these two points of view can be made apparent by considering singular value decomposition (SVD) of the data, a method that is often used to compute PCA. SVD performs the factorization $$D = U\Sigma V^T \quad (6)$$

If D is an m×n matrix, then U and V are m×m and n×n orthogonal matrices, respectively, and Σ is an m×n diagonal matrix containing the singular values along the diagonal, ordered by decreasing size. The right singular vectors V provide abstract representations of the spectra of the individual chemical components (e.g., elements or phases). The min(m, n) singular values are related to the amount of variance in the data that is accounted for by the corresponding principal components. Specifically, the $i^{th}$ singular value is equal to the square root of the variance accounted for by the $i^{th}$ principal component. The diagonal form indicates that the transformed data are uncorrelated. By decomposing the data into a set of uncorrelated factors of decreasing statistical significance, data compression can be accomplished by selecting those factors having the greatest statistical significance and discarding the rest as noise or error.

SVD has the useful property that the space spanned by the first p columns of V represents, in a least squares sense, the best rank-p approximation to the space spanned by the rows of D. The remaining n−p columns of V represent experimental noise or error and can be discarded. Thus, the scores and loading matrices can be truncated, or compressed, to contain only those vectors corresponding to significant singular values. Letting $V_p$ be the matrix whose columns are the first p columns of V, a p-component PCA model can then be computed, according to $$P_p = V_p \quad (7)$$
$$T_p = (U\Sigma)_p$$

where the columns of $P_p$ are mutually orthonormal and those of $T_p$ are mutually orthogonal. Similarly, the space spanned by the first p columns of U represents, in a least squares sense, the best rank-p approximation to the space spanned by the columns of D. The remaining m−p columns of U represent experimental noise or error and can be discarded. Thus, an alternative PCA factorization of D is $$\overline{P}_p = U_p \quad (8)$$
$$\overline{T}_p = (V\Sigma)_p$$

where, again, the columns of $\overline{P}_p$ are mutually orthonormal and those of $\overline{T}_p$ are mutually orthogonal. Transposing Eq. (6) and comparing with Eq. (5) shows the mathematical equivalence of the dual factorizations:

$$D^T = V\Sigma U^T = (V\Sigma)U^T = \overline{T}\overline{P}^T \quad (9)$$

In the following discussion, the bars will be dropped for clarity and the loading matrix P will represent vectors that are orthonormal in the spatial domain, unless otherwise noted.

The conclusion that arises from the foregoing discussion is that there are two equivalent and equally valid ways to describe the data matrix D in terms of a PCA model. In the picture provided by Eq. (7), the orthonormal basis is spectral in nature, whereas, the model in Eq. (8) has an orthonormal image basis. The difference between the two points of view is subtle but has major implications. These relate to how properties of orthogonal and orthonormal (i.e., orthogonal and normalized to unit length) vectors differ upon rotational transformation, as will be described below.

While the matrices T and P include all of the information contained in the pure components, they do not do so in a chemically recognizable form. Therefore, a single principal component will not, in general, represent either a pure element or a multi-element phase, but rather, a linear combination of such elements or phases. In other words, there may not be a one-to-one correspondence between a selected principal component and a particular chemical phase or pure element.

For example, physically admissible concentrations must be non-negative, and the pure-component spectra must be greater than the background signal, whereas a general principal component analysis need not be thus constrained. The principal components produced by PCA often have negative values, which presents a spectrum that is difficult for the practicing analyst to understand. Additionally, a major disadvantage of PCA is that the principal components are constrained to be orthogonal, while any chemical phase that contains overlapping spectral peaks or non-specific spectral backgrounds will necessarily be non-orthogonal. Therefore, subsequent post-processing of results obtained from PCA is useful for transforming the abstract principal components into physically meaningful pure components.

Transformation or "rotation" of PCA loading vectors has been commonly employed, particularly in the psychometric community, to obtain more readily interpretable factors. See H. H. Harman, *Modern Factor Analysis,* 3rd Revised ed., The University of Chicago Press, Chicago (1976); M. W. Browne, *Multivariate Behavioral Research* 36, 111 (2001); and M. Forina et al., *J. Chemometrics* 3, 115 (1988). The general goal of such procedures is to "rotate the factors to simple structure." Thus, given a matrix of loading vectors P, a rotation matrix R is sought such that the rotated loadings $\tilde{P}=PR$ are in some sense simpler and hopefully easier to interpret that the original loadings. As is amply demonstrated by the references, many definitions of "simple structure" have been proposed in the literature, and many algorithms are available to determine R such that the simplicity of $\tilde{P}$ is maximized. At a very basic level, however, simplicity just means that there are many zeros in the matrix of loading vectors $\tilde{P}$. A matrix that has perfectly simple structure is one that has one and only one non-zero entry in every row of the matrix.

In the area of spectral image analysis, rotation of the spectral principal components has been used to obtain simpler spectra that may be easier to interpret. Conversely, the present invention uses rotation of the spatial-domain loading vectors to obtain better, more interpretable components in the spectral domain. Accordingly, a rotation matrix R can be determined, for instance, by the Varimax procedure, that maximizes the simplicity of $\tilde{P}$. The inverse rotation can then be applied to the scores matrix T to yield a factor model that fits the original data equally as well as the PCA model. Assuming R is an orthogonal matrix (i.e., a true rotation), then $$D=TP^T=TRR^TP^T=(TR)(PR)^T=\tilde{T}\tilde{P}^T \text{(spectral basis)} \quad (10)$$

$$D=PT^T=PRR^TT^T=(PR)(TR)^T=\tilde{P}\tilde{T}^T \text{(spatial basis)} \quad (11)$$

Interestingly, while the columns of the rotated loading matrix $\tilde{P}$, like those of the original loading matrix P, are mutually orthonormal, the columns of $\tilde{T}$ have lost the orthogonality present in the original scores matrix T. The implication of this result is that rotation allows the spatial and spectral orthogonality imposed by PCA to be relaxed in either the spatial domain through Eq. (10) or in the spectral domain via Eq. (11).

The key observation, now, is that while spectra are rarely orthogonal, that is, pure-component spectra typically overlap either one another or non-specific backgrounds, samples are often relatively orthogonal in a spatial sense. That is, in a sample with discrete chemical phases X and Y, and assuming boundary pixels make up a small fraction of the total, any particular pixel is likely to represent either phase X or phase Y, but not both. This observation suggests that the factorization approach indicated by Eq. (11) will be effective for the spectral image analysis of a large and important class of analytical problems having spatially simple structure (i.e., substantially comprising pure pixels).

In FIG. 1 is shown a comparison between the PCA and spatially rotated PCA factor solutions for an uncomplicated two-component spectral image. The sample is a Cu/Ni diffusion couple that was imaged by Energy Dispersive X-ray (EDS) analysis in a scanning electron microscope. The sample was imaged at 7 keV yielding only a single, overlapping spectral feature for each element. In FIG. 1(*a*) are shown the measured spectral image (top) and the true pure-component spectra (bottom) for the sample. Since, in this case, the pixels on the left- and right-hand sides of the sample image are known to be pure nickel and pure copper, respectively, the true pure-component spectra were easily derived by simply averaging spectra in these regions of the image. In FIG. 1(*b*) is shown the standard PCA solution for this sample. This solution is abstract; both the abundance information contained in the PC2 vs PC1 plot of the spatial components (top), and the spectral components (bottom) have significant negative intensities. In FIG. 1(*c*) are shown the corresponding PC2 vs PC1 plot (top) and spectral components (bottom) for the rotated PCA solution. After spatially rotating the PCA solution using the Varimax procedure, the centroids of the two spatial component distributions have moved toward the rotated coordinate axes (i.e., the vertical axis corresponds to Ni and the horizontal axis corresponds to Cu). Further, the estimates of the pure-component spectra resemble, but are not quantitatively the same as, the corresponding true pure-component spectra.

The Cu/Ni diffusion couple does not represent a sample with perfectly simple structure. The presence of mixed composition pixels in the diffusion zone introduces a bias into the results. For instance, the centroids of the abundance distributions in the PC2 vs PC1 plot in FIG. 1(*c*) are slightly negative rather than zero. This bias can be compensated for in a subsequent refinement step as will be demonstrated later.

Figure 2:
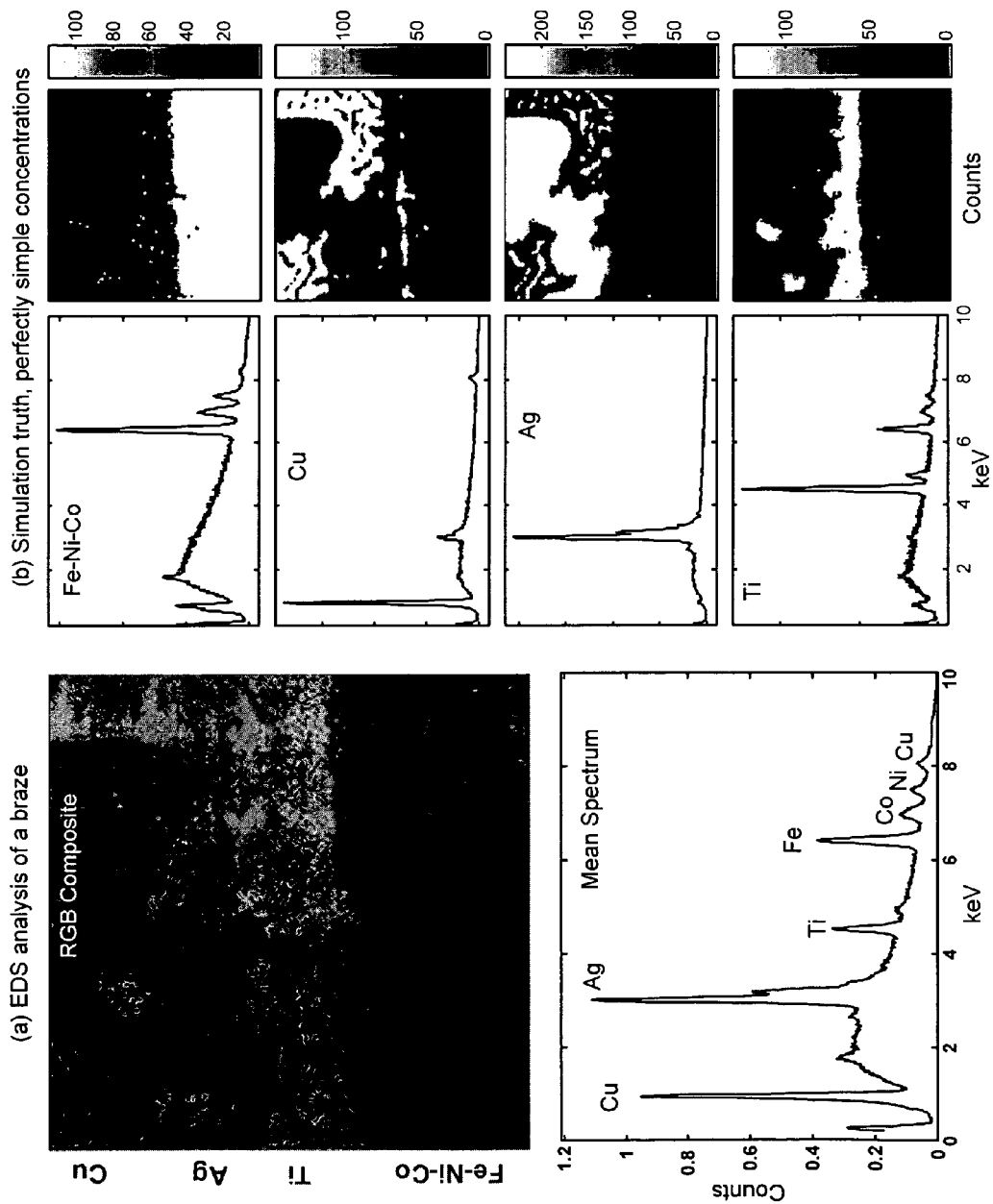
FIG. 2 shows a simulation derived from an actual EDS spectral image of a braze interface.

A simulation can be used to show that no bias is introduced in a sample that does, in fact, possess perfectly simple structure. In FIG. 2 is illustrated a simulation derived from an actual EDS spectral image of a braze interface. As shown in FIG. 2(*a*), to simulate a spatially simply structure, each pixel in the spectral image (top) was assigned to only one of the four chemical phases (i.e., Fe—Ni—Co, Cu, Ag, or Ti). The mean spectrum (bottom) for the composite sample is also shown in FIG. 2(*a*). The true pure-component spectra were defined as the spectral averages over the pixels in each of the four chemical phases. In FIG. 2(*b*) are shown the true pure-component spectra and the abundance maps for each phase.

Figure 3:
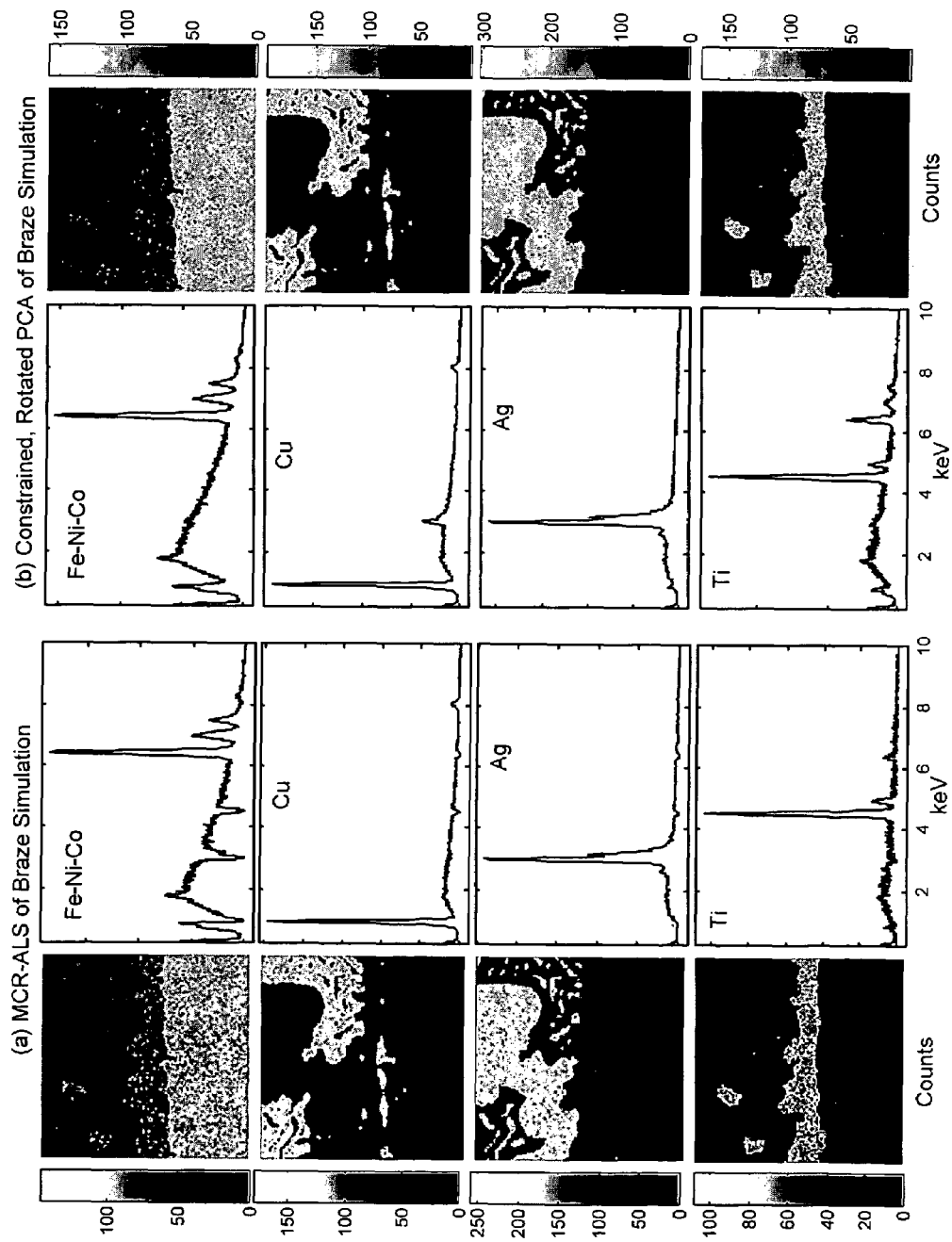
FIG. 3(a) shows the estimated pure-component spectra and abundance maps of the simulated braze interface obtained using a MCR-ALS method.
FIG. 3(b) shows the estimated spectra obtained after rotation of the PCA loadings in the spatial domain and the corresponding abundance maps obtained from a non-negativity-constrained classical least squares analysis using the estimated spectra.

In FIG. 3(*a*) are shown the estimated pure-component spectra and abundance maps of the simulated braze interface shown in FIG. 2(*a*), obtained using the MCR-ALS method of Keenan and Kotula. In this case, non-negativity is not an effective constraint, since there is a large non-specific spectral background. Several estimated spectra exhibit spectral features that, while strictly non-negative, are unphysically negative with respect to the background (e.g., the inverted spikes in the estimated Fe—Ni—Co spectrum). Thus, the MCR-ALS method yields less than satisfactory results.

However, the factorization approach of Eq. (11) yields improved results. In FIG. 3(*b*) are shown the estimated pure-component spectra obtained after rotation of the PCA loadings in the spatial domain. These agree with the true pure-component spectra, shown in FIG. 2(*b*), within the noise. This improvement is possible, because the simulated braze interface has a spatial structure that is perfectly simple. The abundance maps in FIG. 3(*b*) for the braze simulation were computed by non-negativity constrained classical least squares, given the data and the spectral estimates resulting from the factor rotation procedure. While not strictly necessary here, this approach eliminates noise-induced negative abundances. The agreement with the known abundances shown in FIG. 2(b) is excellent.

Refining the Rotated PCA Solution

As demonstrated by the foregoing discussion regarding spatially simple samples, excellent spectral estimates can be achieved by first rotating spatial-domain loading vectors to simple structure and then applying the same rotation (for the case of an orthogonal R) to the scores matrix. The pure-component concentration estimates, on the other hand, are still constrained to be orthogonal, which can introduce bias into the results if the samples are not perfectly simple. Frequently, these biases can be compensated by imposing additional constraints, non-negativity for instance, on the derived components subsequent to factor rotation.

Return now to the Cu/Ni diffusion-couple sample shown in FIG. 1. This sample does not have a perfectly simple structure, due to the presence of mixed composition pixels in the diffusion zone. The bias introduced by the spatial orthogonality constraint is evidenced by the facts that the centroids of the two rotated spatial components in FIG. 1(c) are negative.

Figure 4:
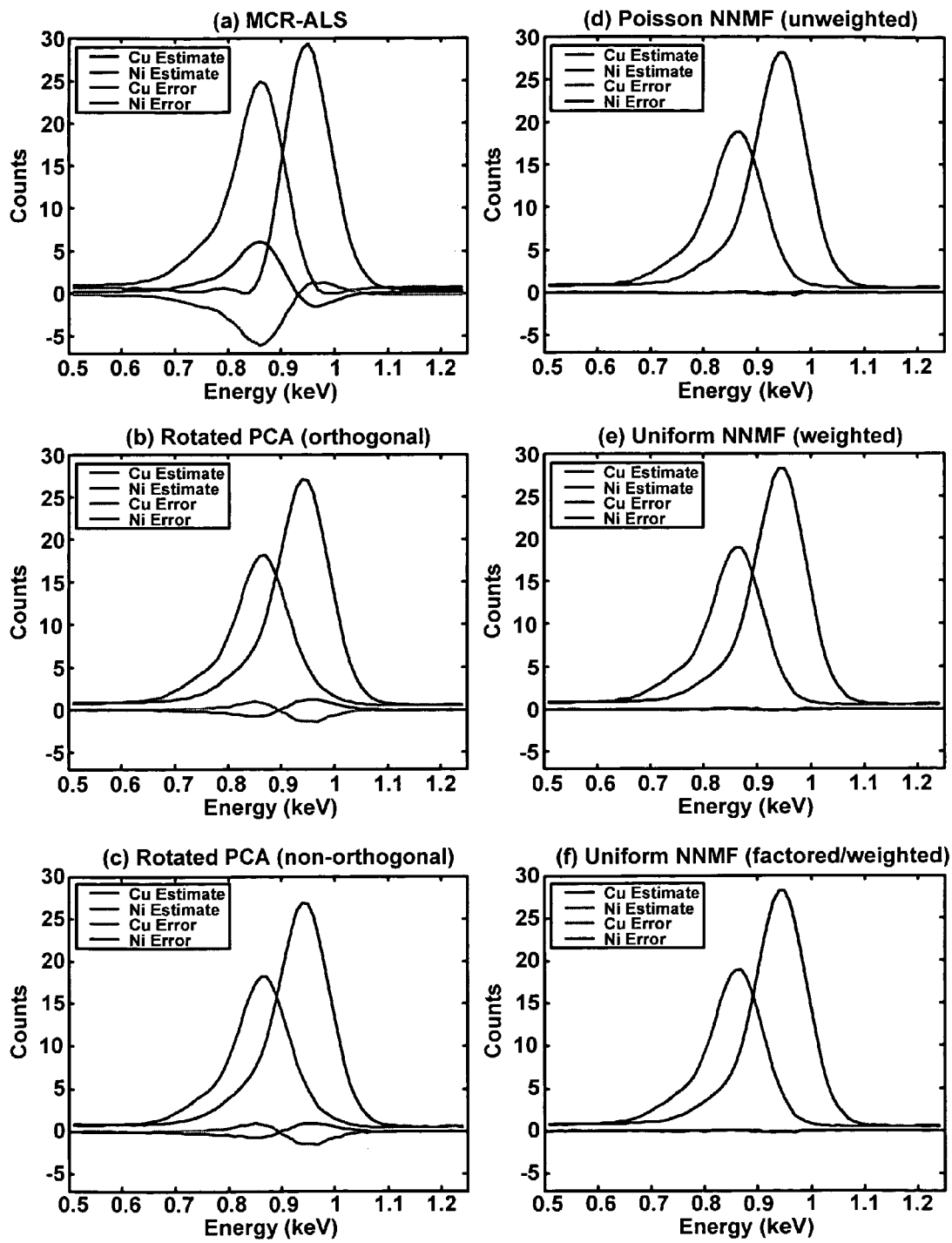
FIG. 4 show spectral estimates obtained from different analyses of the Cu/Ni diffusion couple sample.

In FIG. 4(a) is shown the spectral estimates resulting from an MCR-ALS analysis of the Cu/Ni diffusion couple sample shown in FIG. 1. These estimates are strongly biased in the region of spectral overlap. Therefore, both the estimated Cu spectrum and the estimated Ni spectrum show large errors from the true pure-component spectra in the region of spectral overlap. More accurate spectral estimates are obtained from spatially rotated PCA as shown in FIGS. 4(b) and 4(c), although these spectral estimates still show appreciable bias in the region of spectral overlap. The difference between the approaches in FIGS. 4(b) and 4(c) resides in details of the spectral data weighting procedure. Since EDS forms the spectra by a counting process, the data need to be weighted to account for Poisson noise. In FIG. 4(b), the principal components were unweighted and reorthogonalized prior to rotation, whereas, the principal components were rotated in the weighted space and the rotated factors were subsequently unweighted in FIG. 4(c). For this example, both methods gave essentially equivalent results. By rotating after unweighting (i.e., FIG. 4(b)), however, it is possible to obtain orthogonal spatial factors if an orthogonal rotation matrix R is employed.

Further exclusion of bias requires that refinements be made to both the rotated spectral and spatial components. This refinement can be accomplished using algorithms that impose additional constraints. Typically, the refinement requires an iterative algorithm. Small changes in the spatial-domain components will induce changes in the spectral-domain estimates, which induce additional changes in the spatial components, and so on. For example, the refinement can be accomplished using an alternating least squares algorithm. Alternatively, a particularly suitable family of algorithms for the case of non-negative concentrations and spectra is the maximum-likelihood-based, non-negative matrix factorization (NNMF) method, which has been further elaborated for Poisson data. See D. D. Lee and H. S. Seung, *Nature* 401, 708 (1999), and P. Sajda et al., *Proc. of the SPIE, Wavelets: Applications in Signal and Image Processing X* 5207, 321 (2003).

While these NNMF algorithms tend to be slower than MCR-ALS, they do not introduce constraint-induced bias as quickly as do constrained-least-squares-based approaches. See U.S. patent application Ser. No. 10/794,538 to Keenan, which is incorporated herein by reference. However, since these algorithms are being used simply as a refinement step, the number of required iterations is small and performance is acceptable. For Poisson data, Sajda et al.'s algorithm can be applied to the rotated factors and spectral data after unweighting (i.e., in physical space). In FIG. 4(d) is shown the results of this approach as applied to the Cu/Ni diffusion couple. There is no significant error in the estimated pure-component spectra compared to the true pure-component spectra. Alternatively, refinement can be accomplished in the weighted space. The purpose of weighting is to make the noise look more uniform so the algorithms designed for uniform gaussian noise are more appropriate. Spectral estimates refined in the weighted space using the full weighted data matrix are shown in FIG. 4(e). Finally, both spatial rotation and refinement can be accomplished using a factored representation of the data in the weighted space. See U.S. patent application Ser. Nos. 10/772,548 and 10/772,805 to Keenan, which are incorporated herein by reference. The spectral estimates computed and refined using a factored representation (8 factors) of the Cu/Ni diffusion-couple data set are shown in FIG. 4(f). All of the last three refinement methods yield estimates of the pure-component spectra that agree quantitatively with the known pure spectra.

Figure 5:
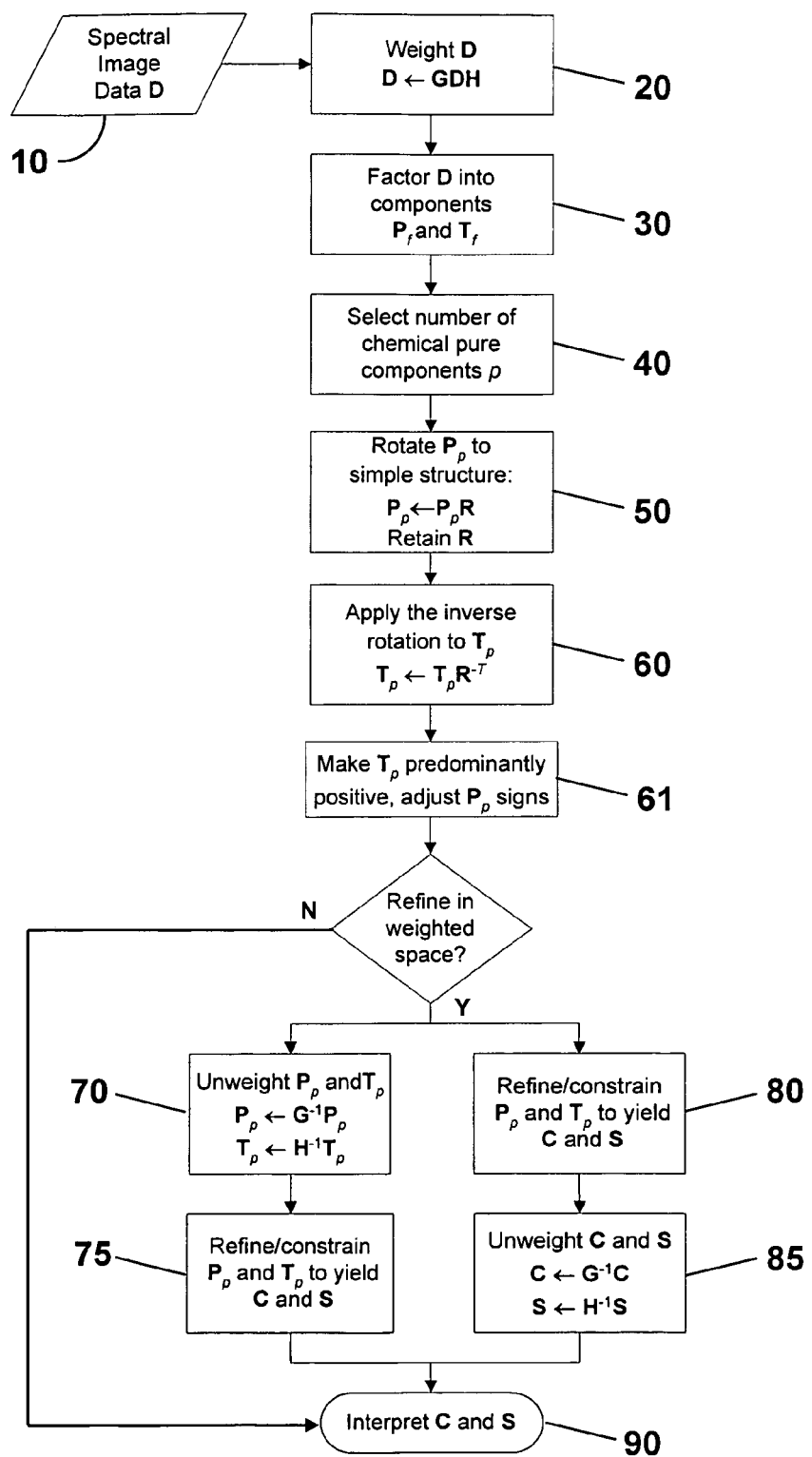
FIG. 5 is a flow diagram for a method for spectral image analysis by exploiting spatial simplicity for the case that the spectral image approximates perfectly simple structure. The data can be presented as the full data matrix D or a factored data matrix of the form $AB^T$.

A Method for Spectral Image Analysis by Exploiting Spatial Simplicity In FIG. 5 is shown a method for spectral image analysis by exploiting spatial simplicity. At step 20 is provided a two-dimensional matrix of spectral image data D. The 2D matrix D can be obtained by unfolding a measured multidimensional spectral data set. Alternatively, the data matrix D at step 10 can be represented as an arbitrary factor model, according to $$D = AB^T \tag{12}$$

where the data factor matrix A comprises spatial information and the data factor B comprises spectral information. At step 20, the data matrix D can be weighted to create a weighted data matrix, according to Eq. (3). For ease of description, the resulting weighted data matrix $\tilde{D}$ can be assigned to data matrix D (as indicated by the ← arrow). At step 30, the data matrix D can be factored using PCA and the resulting components truncated to provide $P_f$ and $T_f$.

Figure 6:
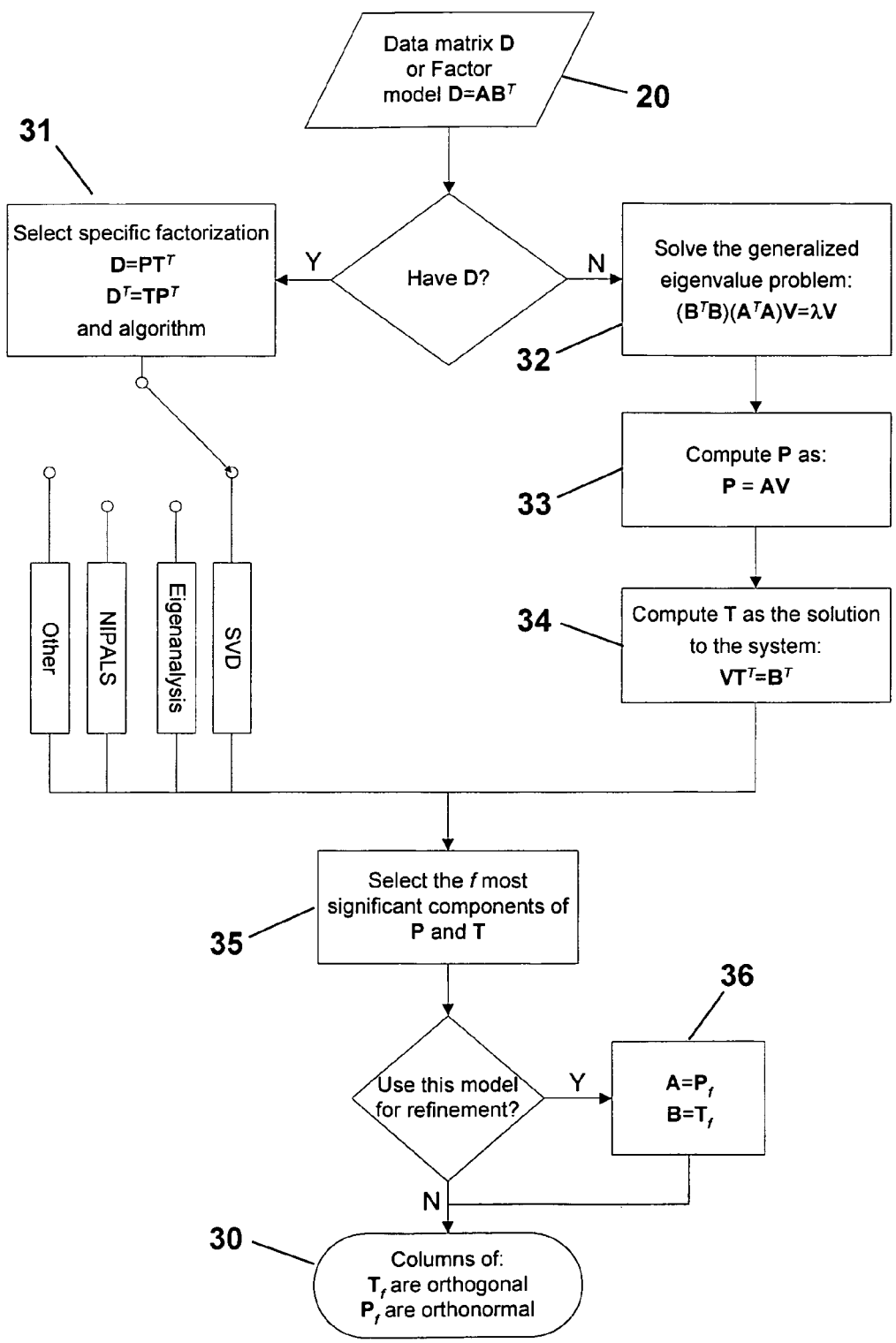
FIG. 6 shows a flow diagram of PCA factorization of D or $AB^T$.

In FIG. 6 is shown the details of PCA factorization, depending on whether the data matrix at step 10 is unfactored or factored. At step 31, PCA can be performed on either the unfactored data matrix D, according to Eq. (4), or the transposed unfactored data matrix $D^T$, according to Eq. (5), using a factorization algorithm. The data matrix is thereby factored into the product of a scores matrix T, whose columns are mutually orthogonal, and a matrix P of orthonormal loading vectors. As is well known to those having skill in the art, there are many algorithms that can be used to perform the PCA factorization, including nonlinear iterative partial least squares (NIPALS), eigenanalysis, and SVD.

For the case that the data matrix is represented in factored form, at step 32, the generalized symmetric eigenvalue problem can then be solved, according to $$(B^T B)(A^T A)V = \lambda V \tag{13}$$

At steps 33 and 34, the PCA model for D can then be computed according to $$P = AV \tag{14}$$

and $T^T$ is obtained as the solution to the set of linear equations:

$$VT^T = B^T \tag{15}$$

The PCA will yield a very large number of principal components. In general, the number of principal components representing noise greatly outnumbers the chemically relevant principal components. Therefore, the f most significant components (e.g., corresponding to the f most significant eigenvalues or singular values) are selected at step 35. It is not necessary to know exactly how many significant components f are needed to represent the chemical information, only that the number of f most significant components selected equals or exceeds the number of chemical pure components p in the sample f>p). See R. Bro and C. Andersson, *Chemometrics and Intell. Lab. Syst.* 42, 105 (1998). Accordingly, at step 35, the loading and scores matrices P and T can be truncated to matrices $P_f$ and $T_f$ by retaining only those vectors corresponding to the f most significant components.

Step 35 generates a factored form of the original data matrix, irrespective of whether the full data matrix D or a factored form of the data matrix, A and B, was provided at step 20. It may be desirable, based on performance considerations, to use this factor model in the subsequent refinement steps. In this case, $P_f$ and $T_f$ can be copied to A and B, respectively, in step 36, and stored for future use. The original truncated principal component matrices, $P_f$ and $T_f$, are returned at step 30.

Returning now to FIG. 5, at step 40, the number of pure components p can be selected to provide a loading matrix $P_p$ having mutually orthonormal columns and a scores matrix $T_p$ having mutually orthogonal columns. The appropriate number of pure components p can be estimated, for instance, using the eigenanalysis as described by Keenan and Kotula. At step 50, an orthogonal rotation matrix R can be determined. For example, the rotation matrix R can be determined by one of the Orthomax-family of procedures (e.g., Quartimax or Varimax). The rotation matrix R can be applied to the loading matrix $P_p$ to provide a rotated loading matrix $\tilde{P}_p$ having a maximally simple structure, according to $\tilde{P}_p = P_p R$. For ease of description, the rotated loading matrix $\tilde{P}_p$ can be assigned to the loading matrix $P_p$. At step 60, the inverse rotation can be applied to the scores matrix $T_p$ to provide a rotated scores matrix $\tilde{T}_P$, according to $\tilde{T}_P = T_p R^{-T}$. For ease of description, the rotated scores matrix $\tilde{T}_P$ can be assigned to the scores matrix $T_p$. The data matrix D is thereby described in the spatial basis $\tilde{P}$, according to Eq. (11).

While the rotated loading matrix is maximally simple, the signs of the rotated principal components suffer a sign ambiguity. In the approximately perfectly simple case, the elements of a given score vector (i.e., a column of $T_p$) will be either predominantly negative or predominantly positive. Since we desire non-negative spectral components, the columns of $T_p$ that are predominantly negative along with the corresponding columns of $P_p$ are multiplied by -1 at step 61.

If no refinement of the rotated PCA solution is necessary, the loading vectors matrix can be normalized and assigned to the concentration matrix (i.e., $C \leftarrow P_p$) and the scores matrix can be normalized and assigned to the spectral shapes matrix (i.e., $S \leftarrow T_P$) and these matrices can be interpreted at step 90.

Alternatively, the rotated PCA solution can be further refined. Only the rotated loading matrix can be refined, or both the loading and scores matrices can be refined. The rotated PCA solution can be refined either prior or subsequent to unweighting. At step 70, the rotated PCA solution can be unweighted prior to refinement by recovering the unweighted loading matrix and unweighted scores matrix using the inverse of the pre- and post-multiply weighting matrices, according to $P_p \leftarrow G^{-1} P_p$ and $T_p \leftarrow H^{-1} T_p$. Obviously, the inverse weighting matrices $G^{-1}$ and $H^{-1}$ can be the identity matrix, if the data matrix was not weighted at step 20. At step 75, the unweighted PCA factors $P_p$ and $T_p$ can then be refined using one of the methods described in FIG. 7, yielding the concentration and spectral shapes matrices C and S. Alternatively, the weighted PCA solution can be refined first at step 80 to yield the weighted concentration and spectral shapes matrices, and then these matrices can be unweighted at step 85, according to $C \leftarrow G^{-1} C$ and $S \leftarrow H^{-1} S$.

Figure 7:
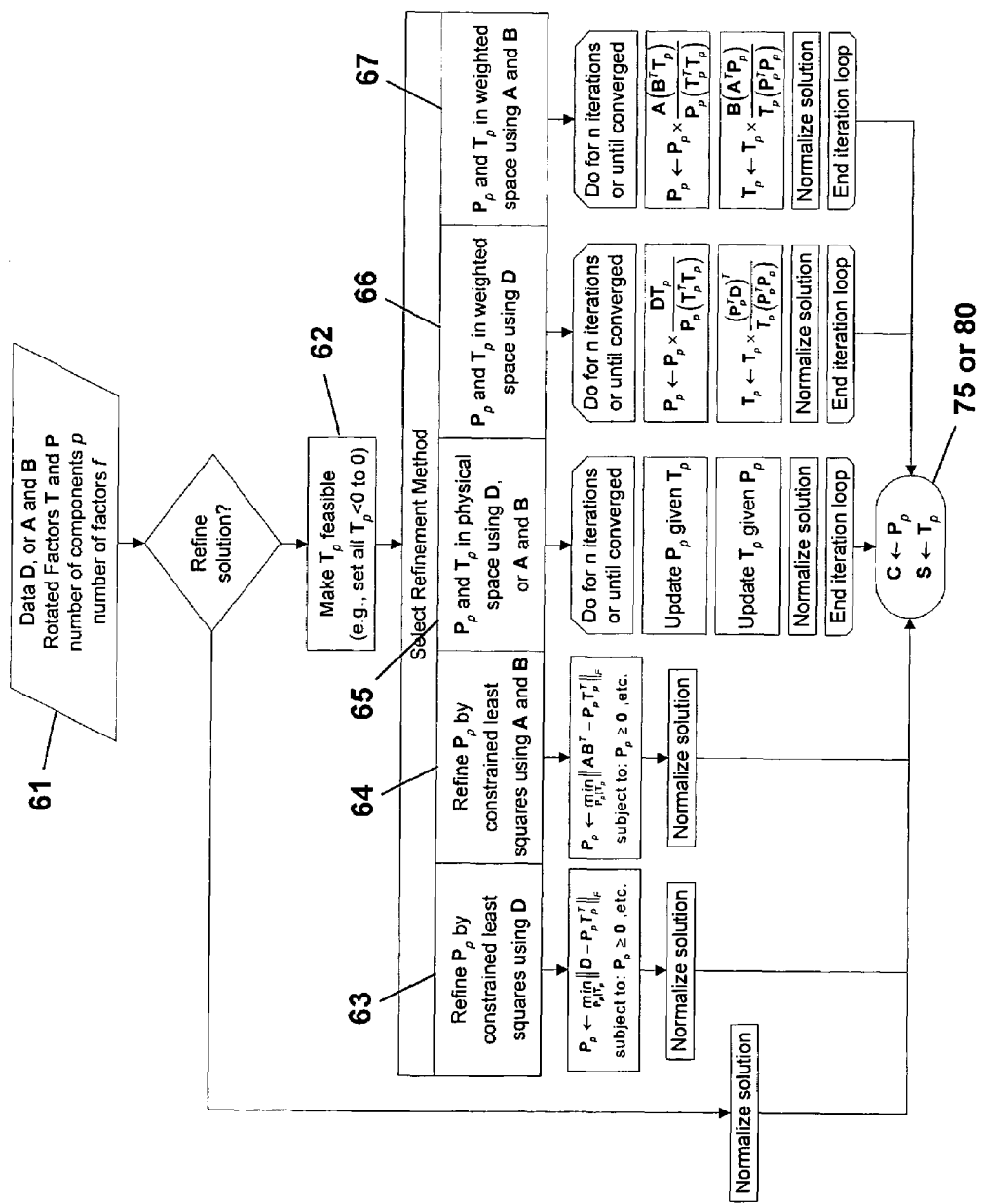
FIG. 7 shows a flow diagram of various approaches to refinement of the rotated PCA solution.

In FIG. 7 are shown a number of methods for refining either the weighted PCA factors $P_p$ and $T_p$ at step 80 or the unweighted PCA factors $P_p$ and $T_p$ at step 75, depending on whether the full data matrix D or the factored representation, A and B, is used for refinement. Component refinement is accomplished by forcing the spectral and abundance components to satisfy physically motivated constraints. For example, physically admissible concentrations and spectra must typically be non-negative. The matrix R was obtained at step 50 by rotating the loading matrix $P_p$ to simple structure for the purpose of obtaining physically realistic and easily interpretable spectral pure components $T_p$ in steps 60 and 61. At step 62, the initial estimate $T_p$ can be made feasible by ensuring that no elements violate the constraints, for instance, by setting the remaining negative matrix elements to zero. Next, as described below, either the spatial or both the spatial and spectral rotated components can be further refined to exclude bias by using algorithms that impose additional constraints.

Step 63 shows a constrained-least-squares approach to refine either the unweighted rotated loading matrix (i.e., at step 75), or the weighted rotated loading matrix (i.e., at step 80), using the data matrix D. The refined loading matrix $P_p$ can be computed from the data and the feasible estimate for the scores matrix $T_p$ by least squares, subject to constraints, according to $$P_p \leftarrow \min_{P_p | T_p} \| D - P_p T_p^T \|_F \quad (16)$$

A common constraint is non-negativity (i.e., $P_p \geq 0$). The refined PCA solution can then be normalized and assigned to the concentration matrix (i.e., $C \leftarrow P_p$) and the spectral shapes matrix (i.e., $S \leftarrow T_P$) at step 75 or 80. If the resulting concentration and spectral shapes matrices C and S are weighted, they can be unweighted at step 85.

Alternatively, at step 64, if the data matrix is represented as an arbitrary factor model (i.e., as $AB^T$) the refined rotated loading matrix can be computed, subject to constraints, according to $$P_p \leftarrow \min_{P_p | T_p} \| AB^T - P_p T_p^T \|_F \quad (17)$$

If the rotated PCA factors have been unweighted at step 70, a refined factorization including refined estimates of both $P_p$ and $T_p$ can be computed, in general, using an alternating sequence of conditional refinements with the data matrix D, according to step 65. One specific refinement algorithm is based on constrained alternating least squares. Given an initial feasible estimate for the scores matrix $T_p$, an updated $P_p$ can be computed, subject to constraints, according to $$P_p \leftarrow \min_{P_p | T_p} \| D - P_p T_p^T \|_F \quad (18)$$

Given this updated $P_p$, an updated $T_p$ can be computed, subject to constraints, according to $$T_p \leftarrow \min_{T_p|P_p} \|D - P_p T_p^T\|_F \qquad (19)$$

The updated PCA factors can be normalized and Eqs. (18) and (19) can be iterated for a predetermined number of iteration loops or until an acceptable level of convergence is achieved. The refined PCA solution can then be assigned to the concentration and spectral shapes matrices at step 75. A similar refined PCA factorization can be computed if the data matrix is represented as an arbitrary factor model.

Figure 8:
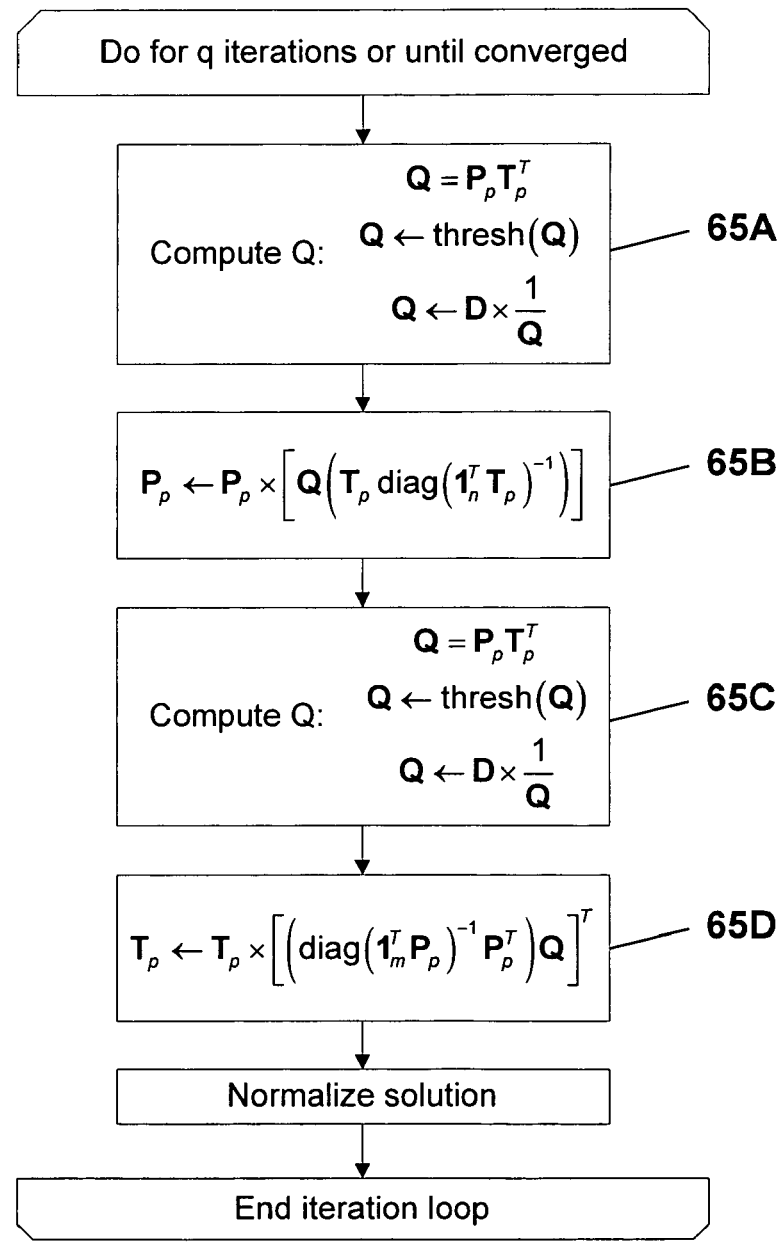
FIG. 8 shows a specific embodiment of step 65 in FIG. 7 for the particular case that the data is Poisson and the full data matrix D is used in the refinement.

A preferred refinement algorithm, at step 65, for the case of Poisson data is the constrained non-negative matrix factorization algorithm of Sajda et al. In FIG. 8 is shown the details of this refinement approach 65. This algorithm is based on an extension of the algorithm of Lee and Seung. The Sajda algorithm naturally imposes non-negativity constraints and is suitable for count data.

At step 65A, the truncated, rotated PCA factors are used to generate a prediction of the data, which is assigned to a matrix Q (i.e., $Q=P_p T_p^T$). The matrix Q can then be thresholded, to disallow values below a certain positive value, such as a noise floor (i.e., $Q \leftarrow \text{thresh}(Q)$). For example, all values below the noise floor can be set equal to a small positive value. The prediction can then be compared with the actual data by taking the element by element quotient $$\left(\text{i.e., } Q \leftarrow D \times \frac{1}{Q}\right).$$

Note that matrix Q will be a matrix of ones, at this point, for the case that the prediction exactly matches the data.

At step 65B, the loading matrix $P_p$ can be updated according to $$P_p \leftarrow P_p \times \left[Q(T_p \text{diag}(1_n^T T_p)^{-1})\right] \qquad (20)$$

where x represents element-wise multiplication. As a given predicted data element deviates from the actual data element, so does the corresponding element of Q differ from one. Thus, elements whose predictions differ most from the actual data experience relatively larger magnitude adjustments during updating.

At step 65C, an updated quotient matrix Q is computed, using the updated $P_p$.

At step 65D, an updated scores matrix $T_p$ can be computed using the updated matrix Q, according to $$T_p \leftarrow T_p \times \left[(\text{diag}(1_m^T P_p)^{-1} P_p^T) Q\right]^T \qquad (21)$$

The updated PCA factors can be normalized and steps 65A-D can be iterated for a predetermined number of iteration loops or until an acceptable level of convergence is achieved. The refined PCA solution can then be assigned to the unweighted concentration and spectral shapes matrices C and S at step 75. This approach was used to refine the estimated pure-component spectra in FIG. 4(d).

Steps 66 and 67 show alternative refinement approaches based on the NNMF algorithm of Lee and Seung. This method iteratively updates the non-negative rotated PCA factors under the assumption of uniform Gaussian noise. For heteroscedastic data, these algorithms are appropriately applied in the weighted space.

At step 66, a refined weighted PCA factorization can be computed using the data matrix D. Given an initial feasible estimate for the scores matrix $T_p$, the loading matrix $P_p$ can be updated, according to $$P_p \leftarrow P_p \times \frac{DT_p}{P_p(T_p^T T_p)} \qquad (22)$$

Given this updated $P_p$, an updated $T_p$ can be computed, according to $$T_p \leftarrow T_p \times \frac{(P_p^T D)^T}{T_p(P_p^T P_p)} \qquad (23)$$

The updated PCA factors can be normalized and Eqs. (22) and (23) can be iterated for a predetermined number of iteration loops or until an acceptable level of convergence is achieved. The refined PCA solution can then be assigned to a weighted concentration matrix (i.e., $C \leftarrow P_P$) and a weighted spectral shapes matrix (i.e., $S \leftarrow T_P$) at step 80. These weighted matrices can be unweighted at step 85, according to $C \leftarrow G^{-1}C$ and $S \leftarrow H^{-1}S$. This approach was used to refine the estimated pure-component spectra in FIG. 4(e).

Alternatively, at step 67, a refined weighted PCA factorization can be computed using a pre-factored data matrix $AB^T$. Given $T_p$, an updated $P_p$ can be computed, according to $$P_p \leftarrow P_p \times \frac{A(B^T T_p)}{P_p(T_p^T T_p)} \qquad (24)$$

With this updated $P_p$, an updated $T_p$ can be computed, according to $$T_p \leftarrow T_p \times \frac{B(A^T P_p)}{T_p(P_p^T P_p)} \qquad (25)$$

The updated PCA factors can be normalized and Eqs. (24) and (25) can be iterated for a predetermined number of iteration loops or an acceptable level of convergence is achieved. The refined PCA solution can then be assigned to a weighted concentration matrix (i.e., $C \leftarrow P_P$) and a weighted spectral shapes matrix (i.e., $S \leftarrow T_P$) at step 80. These weighted matrices can be unweighted at step 85, according to $C \leftarrow G^{-1}C$ and S←H⁻¹S. This approach was used to refine the estimated pure-component spectra in FIG. 4(f).

Spectral Image Analysis by Simplicity-Constrained MCR-ALS

The above description provides methods to analyze imaged samples that are spatially simple and consist of relatively discrete chemical phases. That is, at most pixel locations, it is likely that only one chemical species has a markedly non-zero concentration. PCA loading vector rotation techniques are not effective for analyzing imaged samples having substantial numbers of mixed pixels comprising more than one chemical species. Below is described a method for spectral image analysis of such mixed samples by simplicity-constrained MCR-ALS.

In FIG. 9(a) are shown the pure-component spectra and abundance maps for a simulated six-block spectral image wherein each 50×50 pixel block comprises exactly two of the four chemical phases (i.e., Ag, Fe—Ni—Co, Cu, and Ti, from top to bottom). That is, Ag is found only in the upper left, lower left, and lower center blocks of the spectral image; Fe—Ni—Co is found in the three upper blocks and none of the lower blocks; etc. Therefore, the six blocks represent all combinations of the four phases taken two at a time. Poisson noise was added with a Poisson random number generator and the counting rate was fixed at 500 counts per pixel, on average, for the simulation.

In FIG. 9(b) are shown the estimated pure-component spectra and abundance maps obtained by the spatially rotated PCA method described above. The results are unphysical and difficult to interpret. As with standard PCA, the estimated spectral components exhibit major negative features and the abundance maps do not resemble the known abundance distributions. The failure of the spatially rotated PCA method arises fundamentally from violation of the approximate perfect simplicity assumption. While this simulated spectral image is simple in the sense that 50% of all concentrations are zero, it is not perfectly simple at any pixel.

In FIG. 9(c) are shown estimated pure-component spectra and abundance maps obtained by standard non-negativity constrained MCR-ALS. While considerably better than the estimates obtained by spatially rotated PCA, the abundance maps are still mixed and biased, and the estimated spectra show unrealistic features that are negative with respect to the non-specific background.

Figure 9:
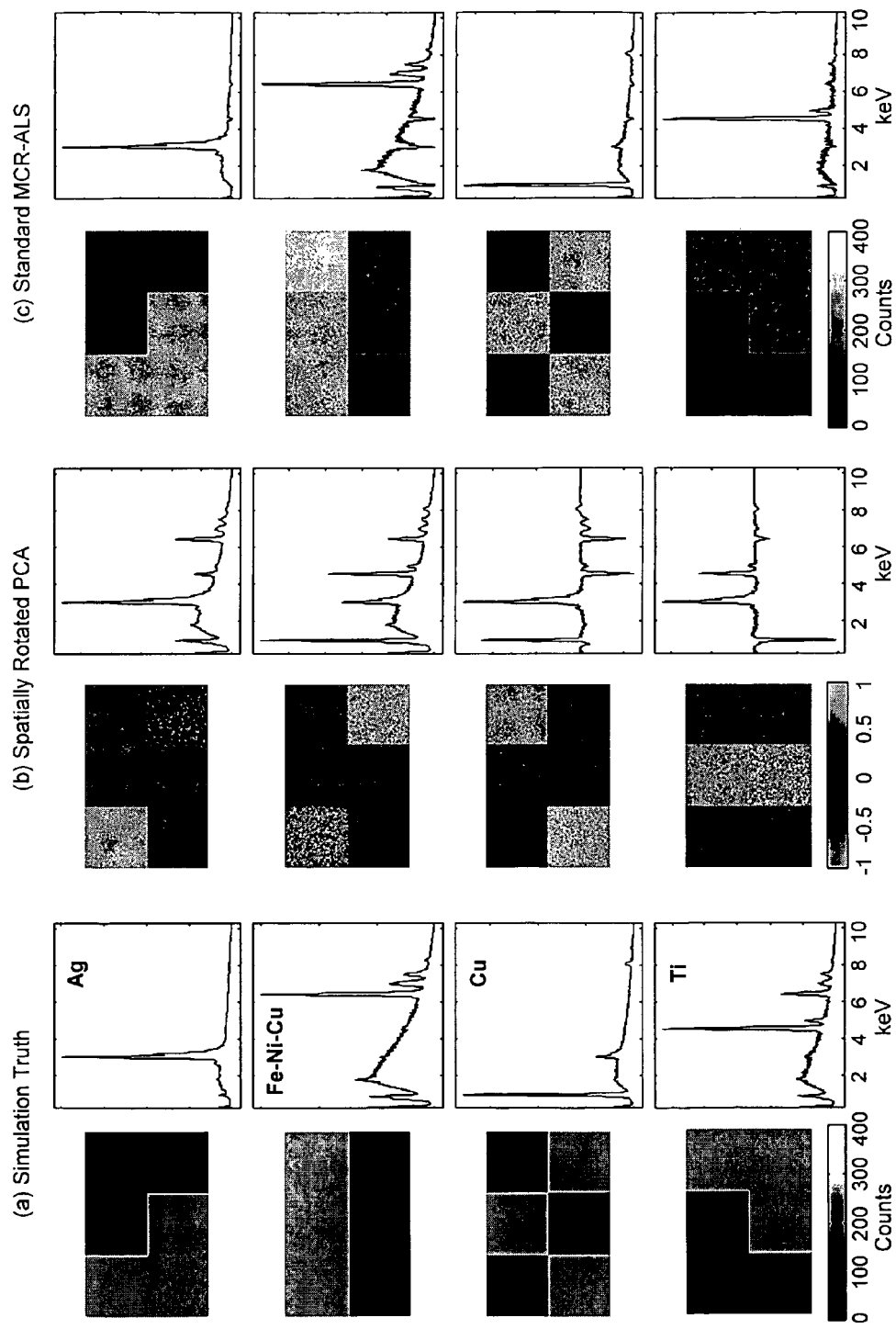
FIG. 9(a) shows a simulation wherein the composition at each pixel is an equal combination of two of the four components comprising the entire sample.
FIG. 9(b) shows the estimated pure-component spectra and abundance maps obtained after rotation of the PCA loadings in the spatial domain.
FIG. 9(c) shows the estimated spectra and abundance maps obtained by a standard MCR-ALS analysis.

It is interesting to note in FIG. 9 that while the true abundances are 50% zeros (i.e., 3 zero-blocks for each of 4 component maps out of 24 blocks total in FIG. 9(a)), visual inspection of the rotated PCA results in FIG. 9(b) finds 8 blocks of 24 to have near-zero concentrations (33% zeros overall) and, similarly, MCR-ALS results in FIG. 9(c) finds 10 blocks of 24 to have near-zero concentrations (42% zeros). This suggests that higher fidelity spectral and abundance estimates could be obtained by forcing the estimated abundances to have a higher proportion of zeros.

Figure 10:
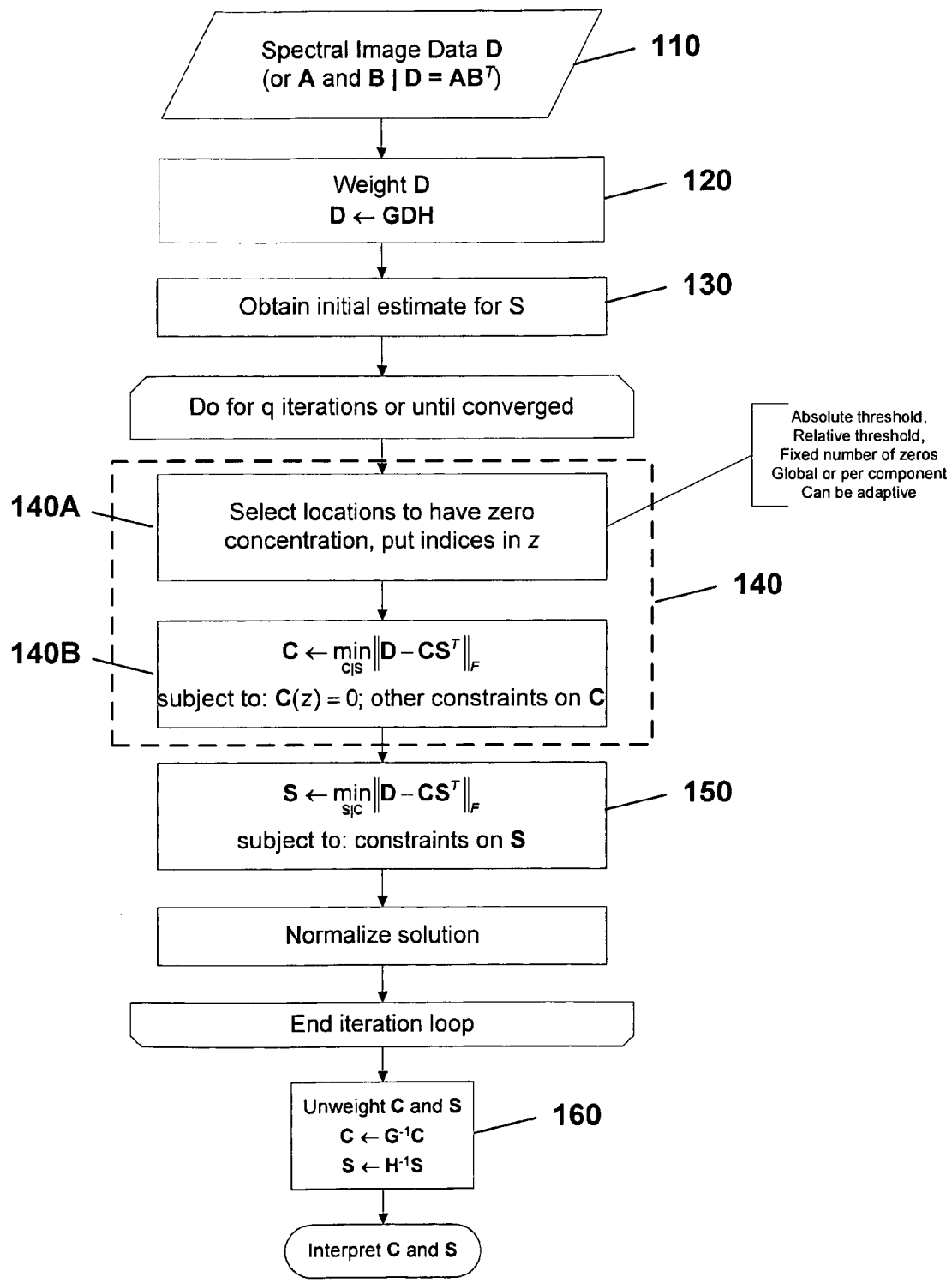
FIG. 10 is a flow diagram for a method of spectral image analysis by imposing spatial simplicity as a constraint during MCR-ALS.

In FIG. 10 is shown a flow diagram for a method of spectral image analysis by simplicity-constrained MCR-ALS. The basic strategy for improved spectral image analysis, in this method, is to incorporate simplicity as an additional constraint during MCR-ALS. At step 110 is provided a two-dimensional matrix of spectral image data D or a factored representation of the data matrix model, comprising data factor matrix A and the data factor matrix B. At step 120, the data matrix can be weighted to create a weighted data matrix. At step 130, an initial estimate is made for the spectral shapes matrix S (for example, uniformly distributed random numbers, or the results of a preliminary analysis).

At step 140, the concentration matrix C is estimated using spatial simplicity constraints in addition to other standard constraints, such as non-negativity. As indicated by the dotted box 140, step 140A of selecting the number and locations of zeros in the concentration matrix C and step 140B of solving the constrained problem can be performed sequentially, or these steps can be interleaved. Further, there are many approaches that can be used to select the number and locations of zero concentration and solving the constrained problem.

Figure 11:
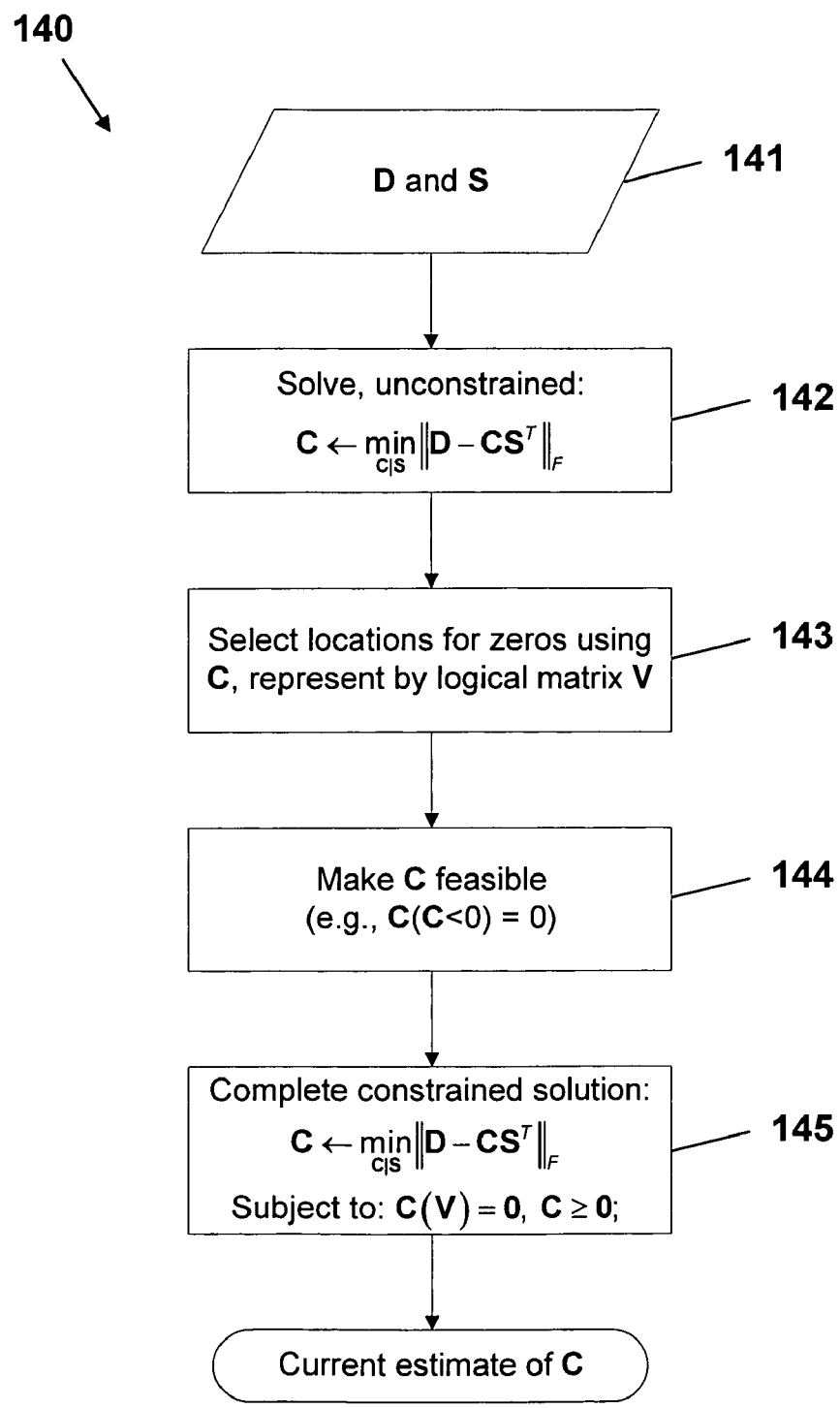
FIG. 11 shows a constrained least squares algorithm that can be used to estimate the abundance matrix using spatial simplicity constraints.

In FIG. 11 is shown an approach for performing step 140. Starting with the data matrix D and the current estimate of the spectral shapes matrix S at step 141, an unconstrained solution for the concentration matrix C can be obtained at step 142, according to $$C \leftarrow \min_{C|S}\|D - CS^T\|_F \qquad (26)$$

This unconstrained solution can be used to estimate the number and locations of zero concentration. Several approaches can be used to select the numbers and locations of the zero matrix elements in the unconstrained solution for the concentration matrix C, including absolute or relative thresholding, fixing the number of zeros, and zeroing the abundance elements globally or on a per component basis. At step 143, the number and locations for the abundance elements in C that are selected to be zero can be represented by a logical matrix V. At step 144, the matrix C is made feasible by setting any remaining negative matrix elements to zero. After identifying the particular abundance elements in matrix C that should be zero, a constrained least squares estimate for C is obtained at step 145:

$$C \leftarrow \min_{C|S}\|D - CS^T\|_F \qquad (27)$$

subject to zero-equality constraints at the particular locations indicated by the logical matrix V, together with other constraints, such as non-negativity, applied to the full matrix. The combined application of equality and inequality constraints (e.g., non-negativity) can be accomplished using the constrained ALS algorithms described in U.S. patent application Ser. No. 10/938,444 to Van Benthem and Keenan, which is incorporated herein by reference.

Returning to FIG. 10, the current estimate of C can then be used at step 150 to obtain a new estimate for the spectral shapes matrix S, subject to constraints, according to $$S \leftarrow \min_{S|C}\|D - CS^T\|_F \qquad (28)$$

The estimates for C and S can be normalized and steps 140 and 150 can be iterated for a predetermined number of iteration loops or until an acceptable level of convergence is achieved. At step 160, the converged solution can be unweighted, according to C←G⁻¹C and S←H⁻¹S.

Figure 12:
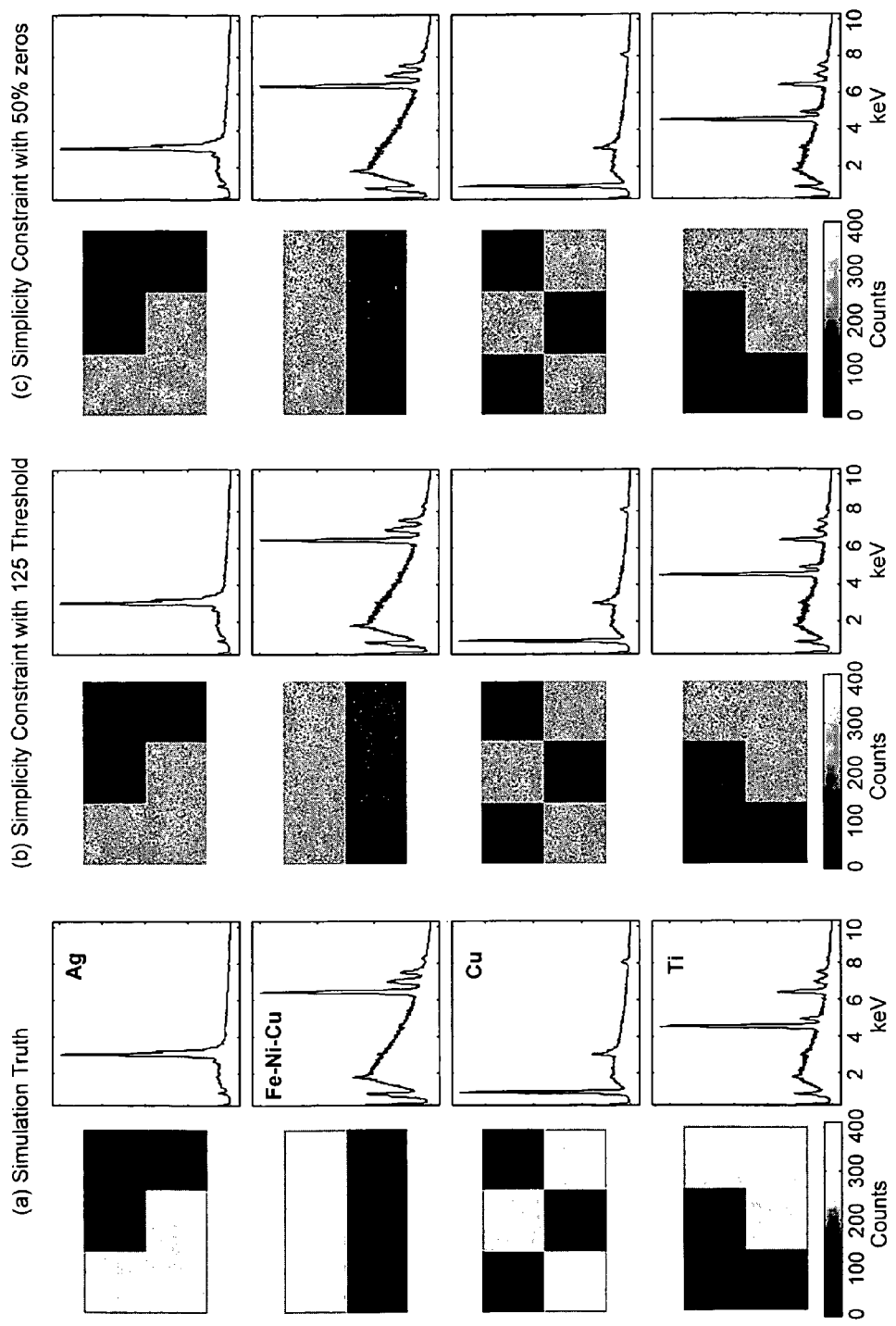
FIG. 12(a) shows a simulation wherein the composition at each pixel is an equal combination of two of the four components comprising the entire sample.
FIG. 12(b) and FIG. 12(c) show the estimated pure-component spectra and abundance maps obtained by imposing a spatial simplicity constraint in MCR-ALS. For the analysis represented in FIG. 12(b), the number of zeros and their locations were selected by thresholding the abundance maps. In the analysis shown in FIG. 12(c), the abundance maps were constrained to contain a fixed number of zeros.

Two approaches are evident for selecting the number and locations of elements in the concentration matrix C, at step 143, that will be constrained to equal zero. First, abundance estimates that are smaller than a threshold value can be constrained to equal zero. The threshold can be an absolute fixed abundance level. Alternatively, the threshold can be relative, for example, component abundances that are less than a certain fraction of the total abundance in a given pixel are constrained to equal zero. The threshold can be global, that is, a single value that applies equally to all components, or a different threshold can be applied to each component. In FIG. 12(b) are shown the abundance and spectral estimates obtained for the six-block simulation using a global absolute threshold of 125 counts. Excellent agreement with the true pure components, shown in FIG. 12(a), is achieved.

The second approach simply sets a fixed number of elements to zero. The number of zeros can be fixed globally, or can be set individually for each component. In FIG. 12(c) are shown the abundance and spectral estimates obtained for the six-block simulation by constraining 50% of the abundance matrix elements to equal zero. Again, excellent agreement with the true pure components is obtained.

Obviously, the number and/or locations of the zeros may vary from iteration to iteration of the MCR-ALS algorithm. As described above, a convenient method for selecting the locations of the zeros uses an unconstrained estimate of the abundance matrix. That is, given the current estimate of the spectral shapes matrix S, an unconstrained estimate of C is obtained by classical least squares at step 142. For the thresholding method, locations of the zeros are identified as those whose unconstrained estimates are smaller than a threshold value. Alternatively, if the absolute number of zeros is to be fixed, the locations of the zeros are chosen to correspond with the fixed number of smallest unconstrained abundance estimates. Since the first step in the constrained least squares algorithm of Van Benthem and Keenan is to obtain an unconstrained solution for C, minor modifications of that algorithm allow the equality-constraint matrices to be computed on-the-fly with little performance penalty.

Figure 13:
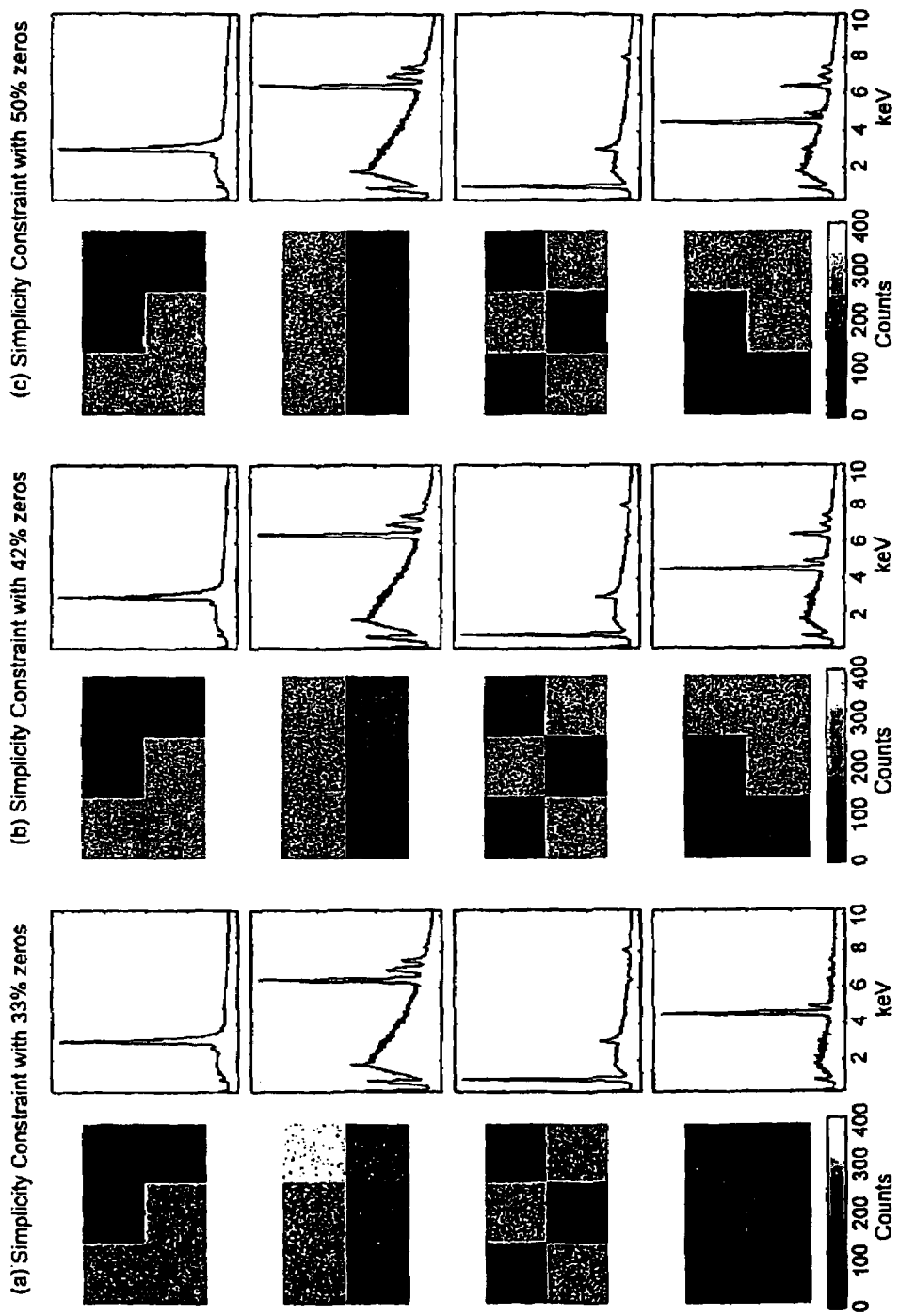
FIG. 13 shows the estimated pure-component spectra and abundance maps obtained for the simulation of FIG. 9 when then number of zeros in a simplicity-constrained MCR-ALS analysis was iteratively adjusted.

The total number of zero abundances in the six-block simulation shown in FIG. 9(a) was known a priori. This will not, in general, be the case. Several methods are available to estimate the appropriate number of elements to be constrained to equal zero. In one approach, the simplicity-constrained MCR-ALS algorithm can be applied iteratively, with a new threshold/number of zeros being set after each iteration. An example of this approach is illustrated in FIG. 13. Returning to the spatially rotated PCA abundance estimates for the six-block simulation in FIG. 9(b), it appears that about 33% of the abundance elements are near zero. In FIG. 13(a) are shown the simplicity-constrained MCR-ALS abundance and spectral estimates obtained by constraining 33% of the abundance elements to equal zero. These new abundance elements appear to have 42% of their elements near zero (10 of 24 blocks). Repeating the simplicity-constrained MCR-ALS algorithm, now with 42% of the abundance elements constrained to equal zero, yields the abundance and spectral estimates shown in FIG. 13(b). It now appears that about 50% of the abundance elements are near zero (12 of 24 blocks). One final iteration of the simplicity-constrained MCR-ALS algorithms with 50% of the abundance elements constrained to equal zero yields the quantitatively correct abundance and spectral estimates shown in FIG. 13(c).

Figure 14:
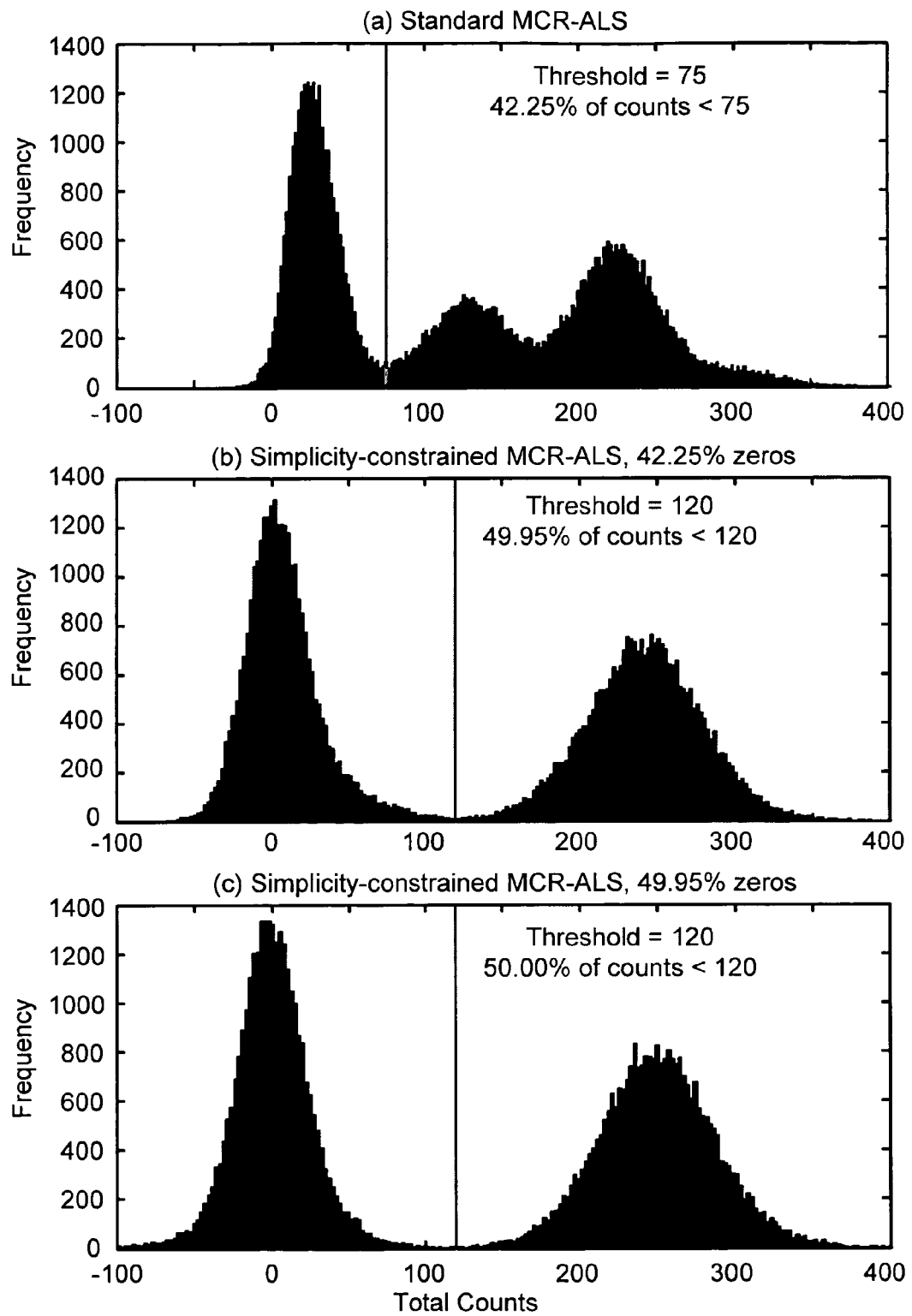
FIG. 14 shows histograms of the estimated total abundances obtained for the simulation of FIG. 9 by unconstrained classical least squares when the spectral estimates were provided by simplicity constrained MCR-ALS.

In the foregoing discussion, the numbers of zeros were selected by visual inspection. Standard image processing techniques can also be used to select the threshold/fixed number of zeros in an automated way, thus enabling an adaptive simplicity-constrained MCR-ALS algorithm. In FIG. 14(a) is shown a histogram of the component abundances for the six-block simulation as obtained by unconstrained classical least squares subsequent to spectral estimation by standard non-negativity constrained MCR-ALS. Assuming the peak in the histogram corresponding to the smallest number of counts represent locations that should be zero, the histogram can be segmented using standard techniques into zero and non-zero components. See, e.g., R. C. Gonzalez and R. E. Woods, *Digital Image Processing*, Second Edition, Prentice Hall, 2002. Either a threshold or number of zeros can be estimated by this approach, as shown. Specifically, about 42.25% of the elements are less than the global absolute threshold of 75 total counts.

This histogram processing approach can also be applied iteratively. In FIG. 14(b) is shown the histogram of the unconstrained abundances using the spectral estimates from simplicity-constrained MCR-ALS with 42.25% zeros. 49.95% of the abundance elements are represented in the histogram peak centered on zero. In FIG. 14(c) is shown the histogram of the unconstrained abundances using the spectral estimates from simplicity-constrained MCR-ALS with 49.95% zeros. These results are quantitatively correct.

Figure 15:
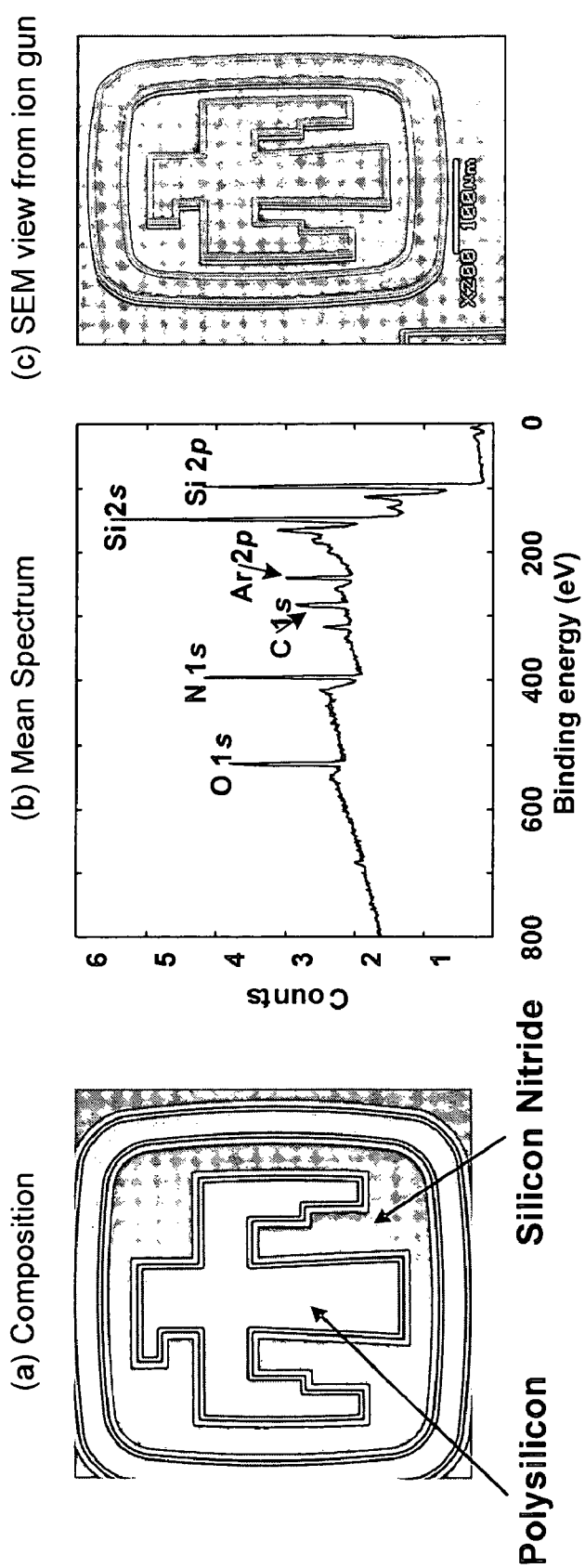
FIG. 15 shows a micro-electro-mechanical (MEMS) device that was imaged by X-Ray Photoelectron Spectroscopy (XPS).

A relative thresholding approach to selecting the numbers and locations of the abundance elements to be constrained to equal zero can be described with reference to the analysis presented in FIG. 15. In FIG. 15(a) is shown a schematic of a sample, which is a MEMS device that is composed of polysilicon on a silicon nitride substrate. The sample was imaged by XPS. FIG. 15(b) shows the mean spectrum obtained by averaging all of the spectra in the 256×256-pixel spectral image. Prior to imaging, a surface oxide was removed by sputtering the sample with argon ions. The sample, which has 3-dimensional structure, was tilted with respect to the ion gun as is shown in FIG. 15(c) As a result, some edges were shadowed during sputtering, leaving the oxide in place.

Figure 16:
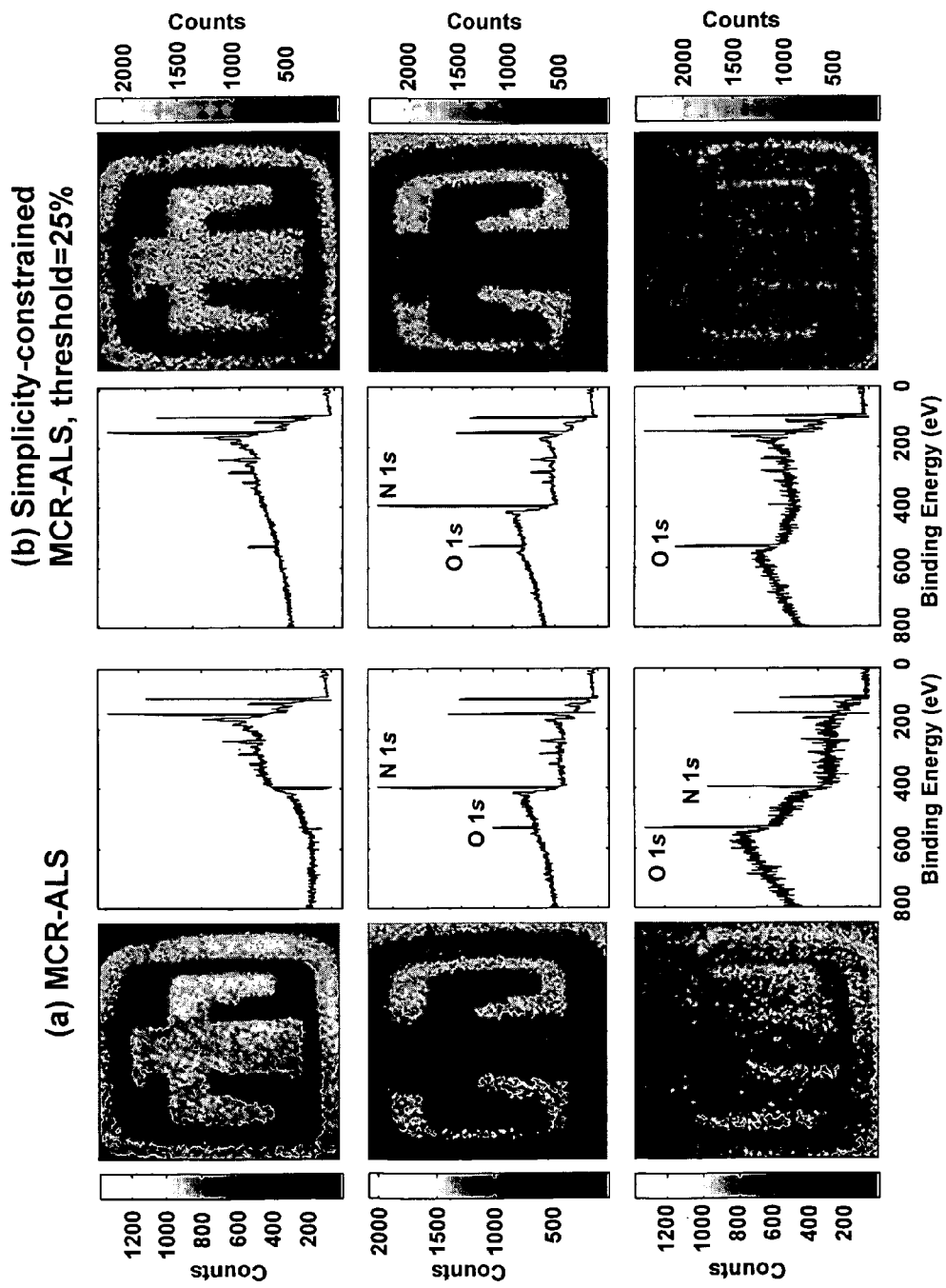
FIG. 16(a) shows the estimated pure-component spectra and abundance maps of the MEMS device obtained by the MCR-ALS method.
FIG. 16(b) shows the estimated pure-component spectra and abundance maps obtained by the simplicity-constrained MCR-ALS method. For each pixel, individual abundance elements that contained less than 25% of the total intensity in that pixel were constrained to equal zero.

FIG. 16(a) shows the pure-component spectra and abundance maps, as estimated by standard non-negativity constrained MCR-ALS for 3 components. The estimated spectra have non-physical shapes and are difficult to interpret. The physical significance of the third (bottom) component is difficult to discern since appreciable intensity is found at most pixels. FIG. 16(b) shows the estimated pure-component spectra and abundance maps, obtained by the simplicity-constrained MCR-ALS algorithm. In this case, at each pixel, any abundance elements that contained less than 25% of the total abundance for that pixel were constrained to equal zero. The resulting spatial components show higher contrast, and the third component is now clearly associated with the shadowed edges where the oxide was not removed. In addition, the estimated spectra have shapes that are typical of XPS spectra and are easily interpreted.

The present invention has been described as methods for spectral image analysis by exploiting spatial simplicity. It will be understood that the above description is merely illustrative of the applications of the principles of the present invention, the scope of which is to be determined by the claims viewed in light of the specification. Other variants and modifications of the invention will be apparent to those of skill in the art.

I claim:

1. A method for analyzing a measured spectral image of a sample by factoring a matrix of spectral image data D according to $D \cong CS^T$, where C is a concentration matrix describing the distribution of pure components at each spatial location of the sample and S is a spectral shapes matrix representation of the pure-component spectra, comprising:

a) measuring a spectral image of the sample with a spectroscopic imaging system, whereby the spectral image is represented by the matrix of spectral image data D;

b) obtaining an initial estimate for the spectral shapes matrix S;

c) selecting elements of zero abundance in the concentration matrix C;

d) obtaining a least squares estimate for C, subject to the zero-equality constraints at the zero abundance matrix elements, according to $$C \leftarrow \min_{C|S} \|D - CS^T\|_F;$$

and e) obtaining a least squares estimate for S, subject to constraints, according to $$S \leftarrow \min_{S|C} \|D - CS^T\|_F.$$

2. The method of claim 1, further comprising repeating steps c) to e) at least once.

3. The method of claim 1, wherein the data matrix D comprises a factored data matrix, according to $D=AB^T$.

4. The method of claim 1, further comprising weighting the data matrix D prior to step b).

5. The method of claim 1, wherein step c) comprises obtaining an unconstrained solution for C, according to $$C \leftarrow \min_{C|S} \|D - CS^T\|_F,$$

to select the elements of zero abundance.

6. The method of claim 1, wherein step c) comprises selecting the location of elements to be zero that have abundance estimates smaller than a threshold value.

7. The method of claim 6, wherein the threshold value is fixed at an absolute abundance level.

8. The method of claim 6, wherein the threshold value is relative to a certain fraction of the total abundance.

9. The method of claim 6, wherein the threshold value is a global value that applies equally to all components.

10. The method of claim 6, wherein the threshold value is applied differently to each component.

11. The method of claim 1, wherein step c) comprises selecting the number of elements of zero abundance to be fixed.

12. The method of claim 11, wherein the number of elements of zero abundance is fixed globally.

13. The method of claim 11, wherein the number of elements of zero abundance is fixed individually for each component.

14. The method of claim 1, wherein step d) further comprises subject the least squares estimate to other constraints applied to the full matrix.

* * * * *